(12) United States Patent
Grant et al.

(10) Patent No.: US 9,211,191 B2
(45) Date of Patent: Dec. 15, 2015

(54) ORTHOPAEDIC STEM WITH PROTRUSION AND ASSOCIATED SURGICAL PROCEDURE

(71) Applicant: DePuy Synthes Products, LLC, Raynham, MA (US)

(72) Inventors: Stuart R. Grant, Warsaw, IN (US); Robin Maisonneuve, Lyons (FR)

(73) Assignee: DePuy Synthes Products, Inc., Raynham, MA (US)

( * ) Notice: Subject to any disclaimer, the term of this patent is extended or adjusted under 35 U.S.C. 154(b) by 82 days.

(21) Appl. No.: 13/657,146

(22) Filed: Oct. 22, 2012

(65) Prior Publication Data

US 2013/0046391 A1 Feb. 21, 2013

Related U.S. Application Data

(62) Division of application No. 12/006,979, filed on Jan. 8, 2008, now Pat. No. 8,308,806.

(60) Provisional application No. 60/879,844, filed on Jan. 11, 2007.

(51) Int. Cl.
*A61F 2/40* (2006.01)
*A61F 2/30* (2006.01)
(Continued)

(52) U.S. Cl.
CPC ............... *A61F 2/40* (2013.01); *A61F 2/30734* (2013.01); *A61B 17/842* (2013.01); *A61B 17/86* (2013.01); *A61F 2002/30092* (2013.01); *A61F 2002/30332* (2013.01); *A61F 2002/30433* (2013.01); *A61F 2002/30571* (2013.01); *A61F 2002/30578* (2013.01); *A61F 2210/0014* (2013.01);

(Continued)

(58) Field of Classification Search
CPC ............... A61B 17/8061; A61B 17/155; A61F 2002/2835; A61F 2002/30433; A61F 2/3859; A61F 2/40; A61F 2/4003; A61F 2/4014
USPC .................... 623/20.35, 20.36, 22.11–23.14; 128/898
See application file for complete search history.

(56) References Cited

U.S. PATENT DOCUMENTS

| 2,947,308 | A | | 8/1960 | Gorman | |
|---|---|---|---|---|---|
| 3,765,034 | A | * | 10/1973 | Johnston | ............... 623/22.4 |
| 4,042,980 | A | | 8/1977 | Swanson et al. | |

(Continued)

FOREIGN PATENT DOCUMENTS

| EP | 1 059 071 A1 | 12/2000 |
|---|---|---|
| FR | 2 880 793 A1 | 7/2006 |

(Continued)

OTHER PUBLICATIONS

Rockwood, "Global™ FX Shoulder Fracture System," DePuy a Johnson & Johnson Company, 1999 © (34 pages).

(Continued)

*Primary Examiner* — David Isabella
*Assistant Examiner* — Ann Schillinger
(74) *Attorney, Agent, or Firm* — Maginot, Moore & Beck, LLP

(57) ABSTRACT

A method of performing joint arthroplasty on a patient with a bone fragment of a bone at least partially separated from the bone in one embodiment includes providing a prosthetic component with a bone connecting portion and a bone fragment portion, implanting the bone connecting portion of the prosthetic component in the bone, and attaching the bone fragment to the bone using the bone fragment portion.

7 Claims, 29 Drawing Sheets

(51) Int. Cl.
 *A61B 17/84* (2006.01)
 *A61B 17/86* (2006.01)
(52) U.S. Cl.
 CPC . *A61F2220/0033* (2013.01); *A61F 2220/0041* (2013.01)

(56) References Cited

U.S. PATENT DOCUMENTS

| | | | |
|---|---|---|---|
| 4,045,825 A | 9/1977 | Stroot | |
| 4,206,517 A | 6/1980 | Pappas et al. | |
| 4,503,847 A | 3/1985 | Mouradian | |
| 4,563,778 A * | 1/1986 | Roche et al. | 623/22.38 |
| 4,605,416 A | 8/1986 | Grobbelaar | |
| 4,865,605 A | 9/1989 | Dines et al. | |
| 4,919,670 A | 4/1990 | Dale et al. | |
| 5,032,130 A * | 7/1991 | Schelhas et al. | 623/22.42 |
| 5,032,132 A | 7/1991 | Matsen, III et al. | |
| 5,092,898 A | 3/1992 | Bekki et al. | |
| 5,314,479 A | 5/1994 | Rockwood, Jr. et al. | |
| 5,358,526 A | 10/1994 | Tornier | |
| 5,507,817 A | 4/1996 | Craig et al. | |
| 5,507,819 A | 4/1996 | Wolf | |
| 5,728,161 A | 3/1998 | Camino et al. | |
| 5,879,400 A * | 3/1999 | Merrill et al. | 623/22.11 |
| 6,120,542 A | 9/2000 | Camino et al. | |
| 6,171,341 B1 | 1/2001 | Boileau et al. | |
| 6,245,112 B1 * | 6/2001 | Doubler et al. | 623/22.41 |
| 6,334,874 B1 * | 1/2002 | Tornier et al. | 623/19.14 |
| 6,398,812 B1 | 6/2002 | Masini | |
| 6,416,553 B1 | 7/2002 | White et al. | |
| 6,558,425 B2 | 5/2003 | Rockwood, Jr. | |
| 6,799,380 B2 | 10/2004 | Afriat | |
| 7,179,259 B1 | 2/2007 | Gibbs | |
| 7,297,163 B2 | 11/2007 | Huebner | |
| 2004/0230311 A1 | 11/2004 | Cyprien et al. | |
| 2007/0219637 A1 | 9/2007 | Berelsman et al. | |

FOREIGN PATENT DOCUMENTS

| | | |
|---|---|---|
| GB | 2 440 911 A | 2/2008 |
| WO | 2006078864 A1 | 7/2006 |
| WO | 2006/126238 A2 | 11/2006 |

OTHER PUBLICATIONS

European Search Report corresponding to European Application No. 14169518.9, dated Jul. 3, 2014 (8 pages).

Australian Examination Report (i.e., Patent Examination Report No. 1) corresponding to Australian patent application No. 2012200276, dated Sep. 3, 2013 (3 pages).

\* cited by examiner

ORTHOPAEDIC STEM WITH PROTRUSION AND ASSOCIATED SURGICAL PROCEDURE

CROSS REFERENCE TO RELATED APPLICATIONS

This application is a divisional application of U.S. application Ser. No. 12/006,979, filed Jan. 8, 2008 (now U.S. Pat. No. 8,308,806 issued Nov. 13, 2012), which claims priority to U.S. Provisional Application No. 60/879,844, filed Jan. 11, 2007, the entire contents of which are both incorporated by reference in their entirety.

TECHNICAL FIELD

The present invention relates generally to the field of orthopaedics, and more particularly, to a method of implanting a bone prosthesis.

BACKGROUND

Many designs for and methods are known to exist for implanting implantable articles, such as bone prostheses. Such bone prostheses include components of artificial joints, such as elbows, hips, knees and shoulders.

One such implantable prosthesis is shoulder prosthesis. During the lifetime of a patient, it may be necessary to perform a total shoulder replacement procedure on a patient as a result of, for example, disease or trauma, for example disease from osteoarthritis or rheumatoid arthritis. Currently, most implantable shoulder prostheses are total shoulder prostheses. In a total shoulder replacement procedure, a humeral component having a head portion is utilized to replace the natural head portion of the upper arm bone or humerus. The humeral component typically has an elongated intramedullary stem, which is utilized to secure the humeral component to the patient's humerus. In such a total shoulder replacement procedure, the natural glenoid surface of the scapula is resurfaced or otherwise replaced with a glenoid component that provides a bearing surface for the head portion of the humeral component.

Various artificial shoulder prostheses with humeral stems are known. Two examples of such prosthesis are shown in U.S. Pat. Nos. 5,728,161 and 5,314,479. The prosthesis of the '161 patent generally includes a shank portion, a head portion and an attachment mechanism for securing the head portion to the shank portion. Some prosthetic shoulders, such as that shown in FIG. 1 of the '161 patent, include one or more fins formed on the body portion of the device. The fins may include suture holes. In other prosthetic shoulders, some or all of the fins do not include suture holes. Such a device is shown in FIG. 1 of the '479 patent. Additional shoulder prosthesis are shown and discussed in U.S. Pat. No. 5,032,132 to Matsen et al.; U.S. Pat. No. 4,865,605 to Dines et al.; U.S. Pat. No. 4,919,670 to Dale et al.; U.S. Pat. No. 5,358,526 to Tornier; U.S. Pat. No. 5,507,817 to Craig et al.; U.S. Pat. No. 4,045,825 to Stroot; and U.S. Pat. No. 4,042,980 to Swanson et al.

Portions of bone in the condylar portions of long bones sometimes fracture requiring the use of a joint prosthesis. The portions of bone need to be reduced during the arthroplasty procedure. For example, shoulder prostheses are sometimes used to repair what is known as a "four part humeral fracture." Such a fracture typically occurs in the proximal region of the humerus. Often, the humeral head, greater tuberosity and lesser tuberosity separate from the humeral shaft, leaving four parts. A shoulder prosthesis may be used to replace the humeral head and provide a point of attachment for the greater tuberosity and lesser tuberosity.

The greater tuberosity and lesser tuberosity are tension-band sutured together to the humerus. The reduction of the greater tuberosity and lesser tuberosity to the humerus may not be sufficient to promote effective healing and union of the fracture.

A method of implanting an improved joint prosthesis for use with condylar fractures is thus desired.

SUMMARY

The present invention provides an orthopaedic implant with a contact surface for contacting the external peripheral of bone fragments such as those containing the lesser tuberosity and the greater tuberosity to urge the greater tuberosity and lesser tuberosity into contact with a long bone such as the humerus such that the fracture is reduced. By maintaining pressure of the fragments onto the long bone, reduction and union can be accomplished at the fracture site. The present disclosure is well suited for use on condylar fractures of the humerus, but may also be used on other long bones such as the femur, tibia, fibula, ulna, or radius.

A prosthesis may be provided within the scope of the present disclosure in which a solitary finger or multitude of fingers may protrude from the proximal body of a long bone, for example, a shoulder stem and extend distally over the cortex of the lesser and greater tuberosities. The fingers can be unitary or modular and can attach to either the proximal face of the stem or the underside of the prosthetic humeral head.

The modular prosthesis with the fingers of the present disclosure can be made of any suitable material and, for example, may be made of titanium. If made of titanium the fingers may be pre-bent with spikes that may be hammered into the bone fragments.

The fingers provide a force to reduce the fracture such that the fingers are in tension pressing the bone fragment against the humerus. The tension may be caused by the use of a resilient material such as titanium or by the use of a memory metal or nitinol that may provide a constant force on the reduction. The force that the finger applies to the joint may be accomplished by pre-bending the fingers or by utilizing materials that move under temperature changes to provide for the movement to provide this constant force, such as memory metals or super-elastic materials such as nitinol.

The fingers of the present disclosure may include openings that accept bone screws or pegs to secure the fingers to the bone fragments and the humerus or may also include openings for receiving cables and sutures to assist in reducing the bone fragments onto the humerus. The screws that are accepted into the openings in the fingers may pass through the fingers and may be secured to the stem of the prosthesis to form a closed construct such as a square.

The shoulder is secured in position anatomically by a group of four muscles that form a rotator cuff around the shoulder joint. These muscles, by way of tendons, connect to the humeral bone. These four muscles are the subscapularis, the supraspinatus, the infraspinatus, and the teres minor. The subscapularis, supraspinatus, infraspinatus, and teres minor pass over the tuberosities, and as such, the protrusion or fingers of the present disclosure are preferably situated such that irritation to the four muscles and ligaments are minimized. Thus, a plurality of spaced apart fingers may be utilized to provide for the positioning of the muscles against natural tissue with minimal irritation to soft tissue.

According to one embodiment of the present disclosure, there is provided a member for attachment of a bone fragment to a prosthetic joint component during joint arthroplasty. The member includes a first portion including a surface for contact with the external periphery of the bone fragment and a second portion adapted for attachment to a prosthetic joint component. The first portion may include a plurality of spaced apart fingers. The first portion may include an internal wall defining an opening through the first portion. The opening may be adapted to receive sutures, cables, and/or bone screws. The surface for contact with the bone fragment may be adapted to closely conform to the bone fragment. The surface for contact with the bone fragment may be adapted to position the bone fragment in its anatomical position. The first portion may include a tapered protrusion for attachment to the prosthetic joint component. The first portion may be adapted for attachment to an articulating component of the prosthetic joint component or to a stem component of the prosthetic joint component. The first portion may have an arcuate shape. The first portion may include a resilient material and may include nitinol or memory metal. The surface for contact with the bone fragment may include a protrusion in the form of, for example a spike, for penetration into the bone fragment.

According to another embodiment of the present disclosure there is provided a prosthesis for use in joint arthroplasty for a joint formed between adjacent first and second bones in which a bone fragment has separated from the second bone. At least the second bone defines a bone canal of the bone. The prosthesis includes a first articulating member adapted to be secured to the first bone and a second articulating member adapted to be secured to the second bone. The second articulating member includes an articulating portion having an articulation surface for articulation with the first member. The second articulating member further includes an insertion portion connected to the articulating portion for at least partial insertion into the canal of the second bone. The second articulating member also includes a fragment portion connected to the articulating portion and/or the insertion portion. The fragment portion includes a surface for contact with the external periphery of the bone fragment. The fragment portion may include a plurality of spaced apart fingers. The fragment portion may include an internal wall defining an opening through the fragment portion. The opening may be adapted to receive sutures, cables, and/or bone screws. The surface for contact with the bone fragment may be adapted to closely conform to the bone fragment. The surface for contact with the bone fragment may be adapted to position the bone fragment in its anatomical position. The fragment portion may include a tapered protrusion for attachment to the prosthetic joint component. The fragment portion may be adapted for attachment to an articulating component of the prosthetic joint component. The fragment portion may be adapted for attachment to a stem component of the prosthetic joint component. The fragment portion may have an arcuate shape. The fragment portion may include a resilient material and may include nitinol or memory metal. The surface for contact with the bone fragment may include a protrusion for penetration into the bone fragment.

According to still another embodiment of the present disclosure there is provided a first articulating member for use with a second articulating member to form a prosthesis for use in joint arthroplasty for a joint formed between adjacent first and second bones in which a bone fragment having an exterior surface has separated from the first bone. The first articulating member includes an articulating portion having an articulation surface for articulation with the second articulating member and an attaching portion connected to the articulating portion for attachment to the first bone. The first articulating member also includes a fragment portion connected to at least one of the articulating portion and the insertion portion. The fragment portion includes a surface for contact with the external periphery of the bone fragment. The fragment portion may include a plurality of spaced apart fingers. The fragment portion may include an internal wall defining an opening through the fragment portion. The opening may be adapted to receive sutures, cables, and/or bone screws. The surface for contact with the bone fragment may be adapted to closely conform to the bone fragment. The surface for contact with the bone fragment may be adapted to position the bone fragment in its anatomical position. The fragment portion may include a tapered protrusion for attachment to the prosthetic joint component. The fragment portion may be adapted for attachment to an articulating component of the prosthetic joint component. The fragment portion may be adapted for attachment to a stem component of the prosthetic joint component. The fragment portion may have an arcuate shape. The fragment portion may include a resilient material and may include nitinol or memory metal. The surface for contact with the bone fragment may include a protrusion for penetration into the bone fragment.

According to still another embodiment of the present disclosure there is provided a shoulder prosthesis for use in shoulder joint arthroplasty for a shoulder joint formed between the humerus and the glenoid cavity of the scapula in which a bone fragment has separated from the humerus. The humerus defines a bone canal of the humerus. The shoulder prosthesis includes a glenoid member adapted to be secured to the glenoid cavity and a humeral member adapted to be secured to humerus. The humeral member includes a head portion having an articulation surface for articulation with the glenoid member. The humeral member further includes an stem portion connected to the head portion for at least partial insertion into the canal of the humerus and a fragment portion connected to at least one of the head portion and the stem portion. The fragment portion includes a surface for contact with the external periphery of the bone fragment. The fragment portion may include a plurality of spaced apart fingers and an internal wall defining an opening through at least one of the fingers. The opening may be adapted to receive sutures, cables, and/or bone screws. The surface for contact with the bone fragment may be adapted to closely conform to the bone fragment. The surface for contact with the bone fragment may be adapted to position the bone fragment in its anatomical position. The fragment portion may include a tapered protrusion for attachment to the prosthetic joint component. The fragment portion may be adapted for attachment to an articulating component of the prosthetic joint component. The fragment portion may be adapted for attachment to a stem component of the prosthetic joint component. The fragment portion may have an arcuate shape. The fragment portion may include a resilient material and may include nitinol or memory metal. The surface for contact with the bone fragment may include a protrusion for penetration into the bone fragment.

According to still another embodiment of the present disclosure there is provided a stem assembly for use in shoulder joint arthroplasty for the shoulder joint formed between a glenoid cavity of a scapula and a humerus in which a bone fragment having an external surface has separated from the humerus. The humerus defines a bone canal of the humerus. The stem assembly includes a head having an articulation surface for articulation with the glenoid cavity and a stem connected to the head for at least partial insertion into the canal of the humerus. The stem assembly also includes a fragment portion connected to at least one of the head and the stem. The fragment portion includes a surface for contact with the external surface of the bone fragment. The fragment portion may include a plurality of spaced apart fingers. At least one of the head and the fragment portion may be integral with the stem. The glenoid cavity with which the articulation surface of the head articulates may be formed by a prosthetic component. The fragment portion may include an internal wall defining an opening through the fragment portion. The opening may be adapted to receive sutures, cables, and/or bone screws. The surface for contact with the bone fragment may be adapted to closely conform to the bone fragment. The surface for contact with the bone fragment may be adapted to position the bone fragment in its anatomical position. The fragment portion may include a tapered protrusion for attachment to the prosthetic joint component. The fragment portion may be adapted for attachment to an articulating component of the prosthetic joint component. The fragment portion may be adapted for attachment to a stem component of the prosthetic joint component. The fragment portion may have an arcuate shape. The fragment portion may include a resilient material and may include nitinol or memory metal. The surface for contact with the bone fragment may include a protrusion for penetration into the bone fragment.

According to still another embodiment of the present disclosure there is provided a method of performing joint arthroplasty on a patient with a bone fragment at least partially separated from the bone. The method includes providing a prosthetic component with a bone connecting portion and a protrusion and attaching the bone connecting portion of the prosthetic component to the bone. The method also includes attaching the bone fragment to the protrusion of the prosthetic component. The attaching may include attaching the cortical portion of the bone fragment to the protrusion. The attaching may include attaching the bone to the protrusion with a screw. The attaching may include attaching the bone to the protrusion with a barb attached to the protrusion. The patient may have a second bone fragment at least partially separated from the bone. The method may further include attaching the second bone fragment to the protrusion of the prosthetic component. Providing a prosthetic component may include providing a prosthetic component with a second protrusion and attaching the second bone fragment may include attaching the second bone fragment to the second protrusion of the prosthetic component.

According to yet another embodiment of the present disclosure there is provided a shoulder joint for use in arthroplasty. The shoulder joint includes a humeral implant having a head and a stem. The humeral implant including a proximal end and a distal end with the head connected to the stem at the proximal end of the humeral implant. The shoulder joint also includes at least one finger connected to the humeral implant. The at least one finger projects outward from the proximal end of the humeral implant and extends toward the distal end.

The device of the present disclosure may include the ability to provide improved tuberosity fragment fixation when encountering, for example, a four part humeral fracture. For example, a shoulder prosthesis may be provided including a humeral stem which is adapted to be secured to the humerus. The humeral stem includes a fragment portion connected to the humeral stem. The fragment portion includes a surface for contact with the external periphery of the bone fragment. The fragment portion urges the bone fragment into compressing or reducing the humerus. Thus, the present disclosure may provide for improved tuberosity fragment fixation.

The device of the present disclosure may further include the ability to provide for improved tuberosity fragment fixation. For example, a humeral stem may be provided with a fragment portion connected to the stem and extending there from. The fragment portion includes a spike or a plurality of spikes that have a surface for contacting the external periphery of the bone fragment. The fracture surface of the bone fragment is urged into reduction with the humerus thereby providing improved tuberosity fragment fixation. Thus, the present disclosure may provide for improved tuberosity fragment fixation.

The device of the present disclosure may further include the ability to improve humeral bone fracture fixation. For example, the fragment portion of the humeral stem includes fingers that have holes in the fingers for receiving sutures and cables. The sutures and cables are used in conjunction with the fingers on the humeral stem to provide for improved humeral bone fracture fixation. Thus, the present disclosure may provide for improved humeral bone fracture fixation during a humeral fracture repair.

The device of the present disclosure may further include the ability to provide for improved bone fracture fixation. For example, a humeral stem may be provided with a fragment portion extending from the humeral stem. The fragment portion includes openings that receive screws. The screws are inserted through the openings in the fragment portion and into the bone fragments. The screws may also be secured to the stem to provide for additional rigidity. Thus, the present disclosure may provide for improved bone fracture fixation.

The device of the present disclosure may further include the ability to provide long term compression of a humeral fracture. For example, a humeral stem may be provided with a fragment portion that is arranged such that the fragment portion provides tension against the fracture when assembled into the humerus. The fragment portion provides a long term compressive force on the fragment to provide fracture reduction and to promote healing and union of the humerus. Thus, the present disclosure may provide for long term compression of the fragment against the humerus.

The device of the present disclosure may further include the ability to provide for long term compression of a humeral fracture. For example, a humeral stem may be provided with a fragment portion made of a memory metal of nitinol. The fragment portion is arranged such that the memory metal fragment portion provides compression of the bone fragments against the humerus. The compressive force of the memory metal or nitinol provides for a linear continual long term compression of the fragment. Thus, the present disclosure may provide for long term compression of the fragment against the humerus to promote bone fracture healing and union.

Other technical advantages of the present disclosure will be readily apparent to one skilled in the art from the following figures, descriptions and claims.

BRIEF DESCRIPTION OF THE DRAWINGS

For a more complete understanding of the present disclosure and the advantages thereof, reference is now made to the following description taken in connection with the accompanying drawings, in which.

DETAILED DESCRIPTION

Embodiments of the present disclosure and the advantages thereof are best understood by referring to the following descriptions and drawings, wherein like numerals are used for like and corresponding parts of the drawings.

Figure 1:
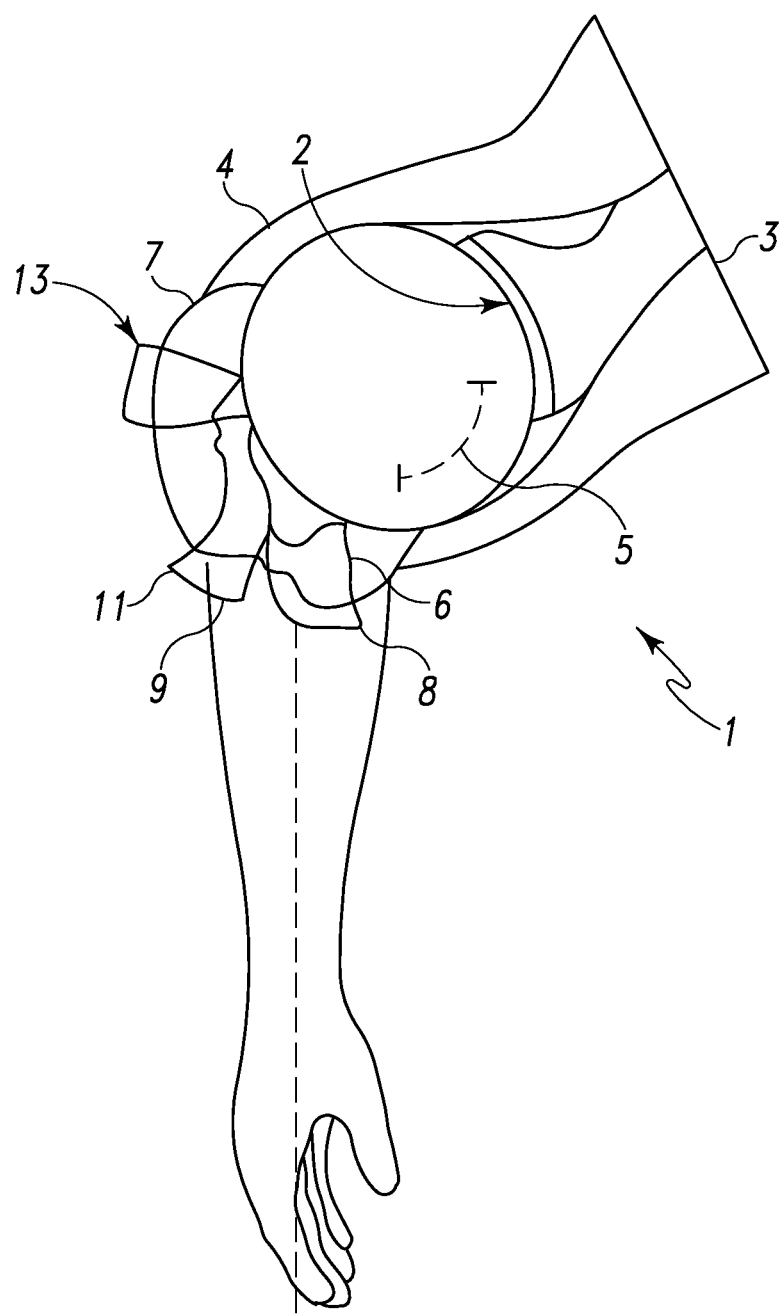
FIG. 1 is a top view of a shoulder in which a prosthesis may be implanted as a part of a joint arthroplasty in accordance with an embodiment of the present disclosure.

Referring now to FIG. 1, a shoulder joint is shown that may utilize a prosthesis with a fragment attachment protrusion member according to the present disclosure. The natural shoulder joint 1, as shown in FIG. 1, is formed between glenoid cavity 2 formed in scapula 3 and head 4 of humerus 5. A series of muscles, tendons, and ligaments extend around and over the head 4 of the humerus 5 to secure the humerus 5 to the glenoid cavity 2 of the scapula 3.

A fracture can occur in the humerus 5. Often in such a fracture, the head 4 separates from the shaft of the humerus 4. For example, one such humeral head fracture is known as a four part humeral fracture. In such a fracture, the head 4 of the humerus 5 fractures, as well as a first bone segment 6 including lesser tuberosity which separates from humerus 5 and a second bone segment 7 including greater tuberosity 7 which also separates or fractures from humerus 5. Thus, the four parts of such a fracture are the shaft of the humerus 5, the humeral head 4, the greater tuberosity bone segment 7, and the lesser tuberosity bone segment 6.

As shown in FIG. 1, the subscaplaris 8 muscles and tendons attach to lesser tuberosity bone segment 6. The teres minor 9 muscles and tendons, as well as the infraspinatus 11 muscles and tendons, attach to the greater tuberosity bone segment 7. Similarly and posteriorly, the supraspinatus 13 muscles and tendons attach to greater tuberosity bone segment 7. The positions of the subscapularis 8, the teres minor 9, the infraspinatus 11, and the supraspinatus 13 are preferably taken into account when designing the shape and size of the protrusions for the prosthesis of the present disclosure. Positioning the protrusions or fingers of the prosthesis of the present disclosure taking these muscles and tendons into account provides for a prosthesis with less muscle and other soft tissue irritation.

Figure 2:
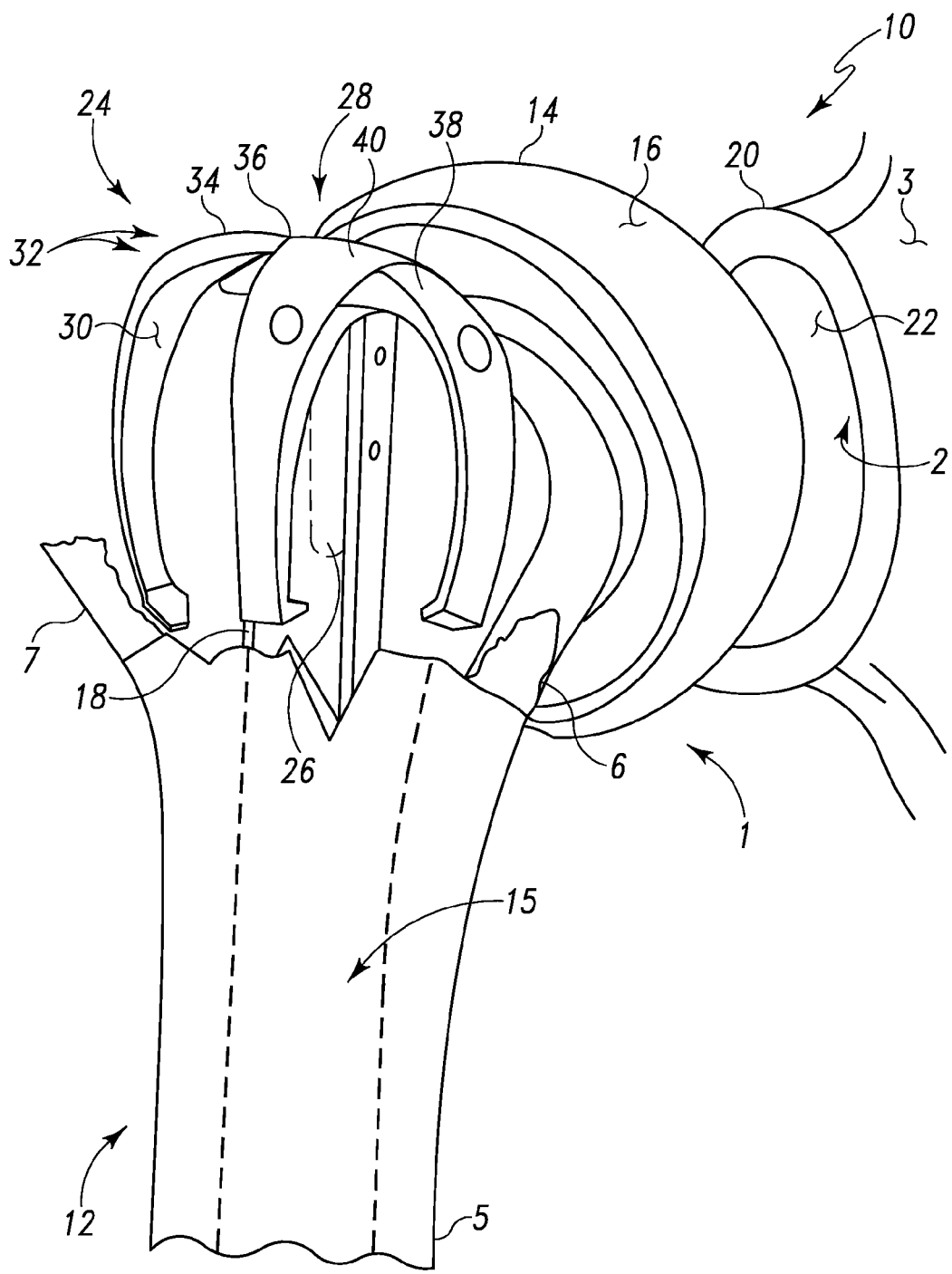
FIG. 2 is a perspective view of a prosthesis with a fragment member in the form of a three fingered protrusion member according to an embodiment of the present disclosure in position in a humerus with a typical four part humeral fracture.

Referring now to FIG. 2, a prosthesis 10 in the form of a shoulder prosthesis is shown. It should be appreciated that a prosthesis with protrusions according to the present disclosure may be utilized in other joints, for example, any other long bone joint, for example, a hip joint, knee joint or similar joint.

As shown in FIG. 2, the prosthesis 10 includes a first articulating member 12. The first articulating member 12 may be in the form of, for example, a humeral stem. The humeral stem may be unitary or modular. It should be appreciated that the first articulating member may be an articulating member that cooperates with a bone other than the humerus and may be utilized in a joint other than the shoulder. The prosthesis 10, of the present disclosure, is adapted for use with fragments of bone that may be found on other fracture sites for other joints, for example, a hip, knee, ankle, elbow, or other orthopaedic joint. If modular, the humeral stem 12 may include a head portion or component 14 which includes an articulating surface 16. The humeral stem 12 may further include an insertion portion in the form of, for example, a stem portion or stem component 18. The stem component 18 may be adapted to at least partially fit within canal 15 of the first bone, or humerus 5.

The humeral stem assembly 12 may cooperate, for example with the natural glenoid cavity 2 or may, as shown in FIG. 2, cooperate with a second articulating member 20. The second articulating member 20 may be in the form of a glenoid component or member. As shown in FIG. 2, the articulating surface 16 of the head component 14 may be convex and cooperate with, for example, a concave surface 22 formed on glenoid member 20.

According to the present disclosure, the humeral stem assembly 12 further includes a protrusion or fragment portion, component, or member 24. The fragment portion 24, it should be appreciated, may be integral with the stem portion 18 and the head portion 14, or may, as is shown in FIG. 2, be a separate component. The fragment component 24 may be connected to the head component 14, or as is shown in FIG. 2, may be connected to the stem component 18. The fragment component 24 may, as is shown in FIG. 2, include a connector 26 which may, as shown in FIG. 2, be a tapered connector. The tapered connector 26 may matingly fit in connector opening 28 formed in stem component 18.

The fragment portion or component 24 may be integral with the humeral stem 12 or may, as is shown in FIG. 2, be a separate component of the humeral stem assembly 12. The fragment component 24 includes a surface 30 for contact with the lesser tuberosity bone fragment 6 and/or the greater tuberosity bone fragment 7. The surface 30 may have a shape that closely conforms to the fragments 6 and 7. The fragment portion 24 includes a finger or a plurality of fingers 32 which extend outwardly and distally from connector 26 of the fragment portion 24. The contact surface 30 of the fragment portion 24, as shown in FIG. 2, is formed on the under side of fingers 32.

As shown in FIG. 2, three separate fingers 32 may be present on the fragment component 24. For example, a posterior finger 34, a middle finger 36, and an anterior finger 38 extend outwardly and distally from the proximal end 40 of the connector 26. The position of the fingers 34, 36, and 38 are preferably selected to accommodate the muscles and ligaments of the shoulder such that minimal soft tissue irritation occurs at the shoulder 1.

Figure 3:
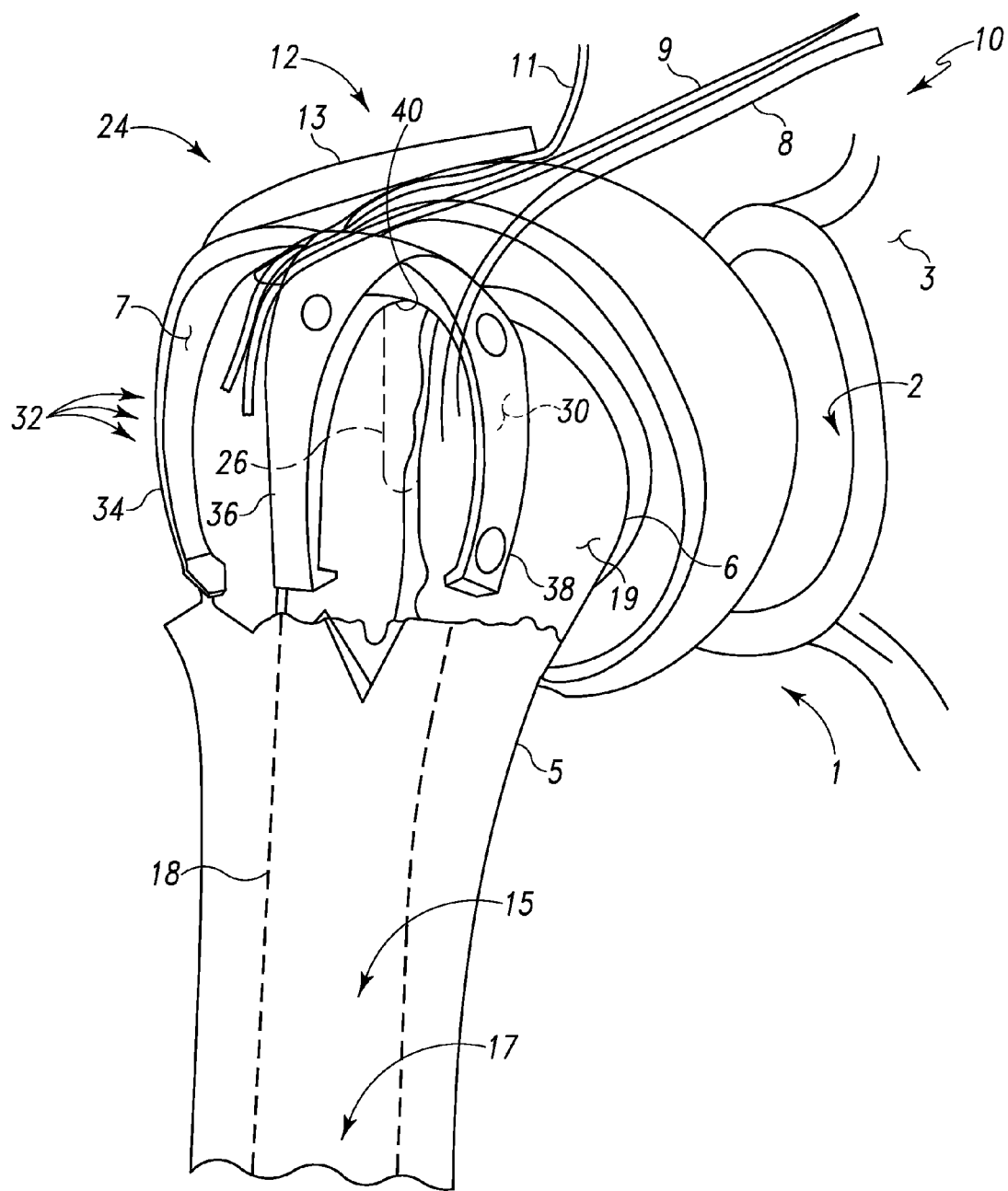
FIG. 3 is another perspective view of the prosthesis of FIG. 2 in position in the humerus with a bone fragment including the greater tuberosity and with a bone fragment including the lesser tuberosity.

According to the present disclosure and referring now to FIG. 3, the soft tissues including the muscles, ligaments, and tendons around the prosthesis 10 of the present disclosure are shown. The fingers 32 of the fragment component 24 are positioned such that lesser tuberosity bone fragment 6 and greater tuberosity bone fragment 7 may be positioned in their anatomical position such that reduction and union can occur in a fracture, for example, in a four part fracture. The convex external periphery 19 of the bone fragments 6 and 7 are positioned such that the internal surface 30 of the fingers 32 closely conform to the external periphery 19 of the fragments 6 and 7. Since the external periphery 19 of the fragments 6 and 7 are generally convex, the internal contact surface 30 of the fingers 32 are preferably concave and preferably have a shape that conforms or matches the anatomical convex external periphery 19 of the fragments 6 and 7.

Figure 4:
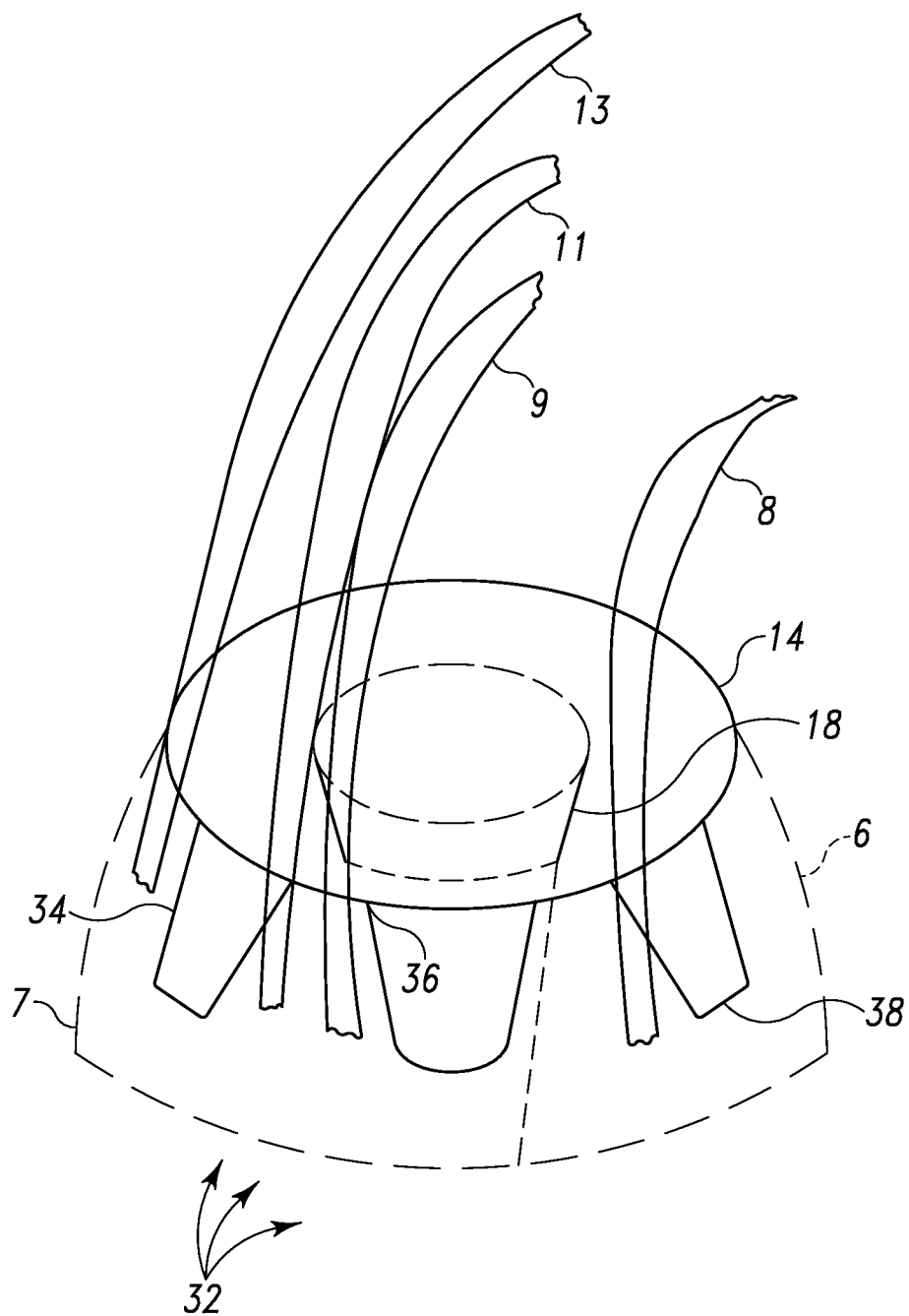
FIG. 4 is a top view of the prosthesis of FIG. 2.

As shown in FIGS. 3 and 4, the posterior finger 34, middle finger 36, and the anterior finger 38, are spaced apart from each other and form a Y or diverge as they extend from proximal end 40 of the connector 26 of the fragment portion 24. The positioning of the fingers 32 is preferably arranged so that minimal soft tissue irritation occurs at the joint or shoulder 1.

For example and as shown in FIGS. 3 and 4, the subscapularis 8 is positioned between anterior finger 38 and middle finger 36. The subscapularis 8 is attached to the lesser tuberosity bone fragment 6. The infraspinatus 11 and the teres minor 9 are attached to the greater tuberosity bone fragment 7 and may be positioned adjacent to each other. The infraspinatus 11 and the teres minor 9 may, as shown in FIG. 3, may be positioned between middle finger 36 and posterior finger 34. The supraspinatus 13, like the infraspinatus 11 and the teres minor 9, is connected to the greater tuberosity bone fragment 7.

The supraspinatus 13 may, as shown in FIG. 3, be positioned posterior to the posterior finger 34. It should be appreciated that the supraspinatus may be positioned between, for example, the posterior finger 34 and the middle finger 36. It should also be appreciated that the soft tissues including muscles and tendons may be positioned with wherever appropriate with respect to the fingers 32 to minimize soft tissue irritation.

Figures 5, 5A:
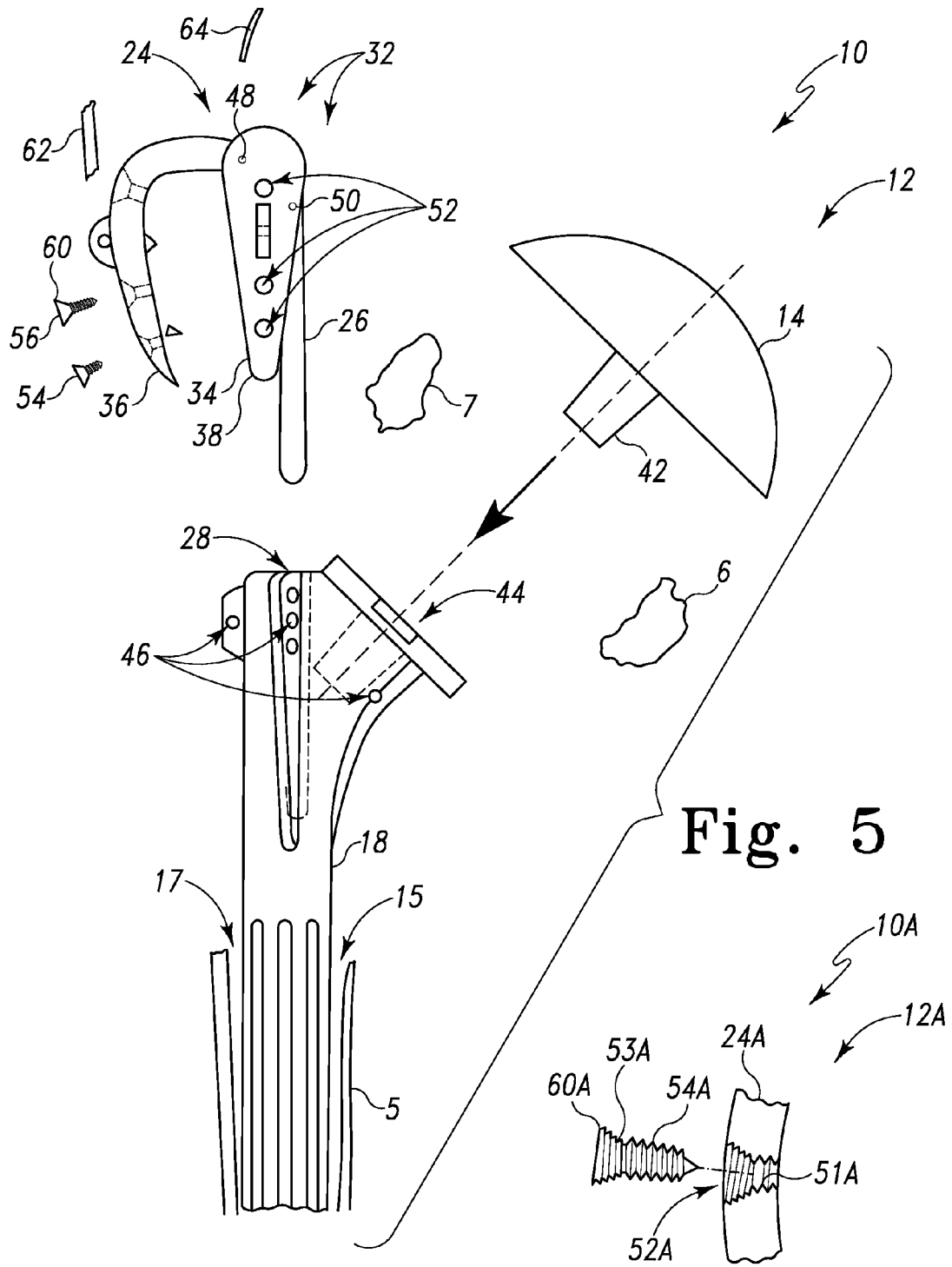
FIG. 5 is an exploded plan view of the prosthesis of FIG. 2.
FIG. 5A is a partial plan view partially in cross section of a fragment member with a rigid screw construction according to another embodiment of the present disclosure.

Referring now to FIG. 5, the humeral stem assembly 12 for use in the prosthesis 10 is shown in an exploded view. As shown in FIG. 5, the humeral stem assembly 12 includes the stem component 18 which is fitted into humeral cavity 17 formed in intramedullary canal 15 of the humerus 5. The humeral stem assembly 12 further includes the head component 14 which is connected to the stem component 18. The head component 14 may include an external taper 42 which is fitted into internal taper 44 formed in stem component 18.

The humeral stem assembly 12 further includes the fragment component 24 which includes a connector 26. The connector 26 may be fitted into opening 28 formed in stem component 18. It should be appreciated that the humeral stem assembly 12 may be preassembled prior to insertion into the body during shoulder surgery or may be assembled in situ in the patient. The ability to assembly the humeral stem assembly 12 in situ may facilitate minimally invasive surgery providing smaller incisions and less soft tissue damage.

The stem component 18 may include a plurality of apertures or openings 46. The openings 46 may be used in connection with sutures and cables to secure soft tissue and bone fragments to the humerus 5.

The fragment component 24 may include suture openings 48 positioned in, for example, the fingers 32. The fragment component 24 may further include cable openings 50 for receiving cables. Typically, cable openings 50 are larger than suture openings 48 to accommodate the larger size of cables. Sutures may be fitted into the cable openings and cables may be fitted into suture openings, if large enough. Multiple sutures and/or cables may be fitted into an opening if room permits. The fragment component 24 may further include openings 52 for receiving pegs or screws, for example, cortical screws 54 and cancellous screws 56. The screws may have locked or unlocked heads. It should be appreciated that the screw openings 52 may include chamfers 58 for providing a recess for the heads 60 of the screws 54 and 45 to minimize soft tissue damage.

The greater tuberosity bone fragment 7 and the lesser tuberosity bone fragment 6 may be secured to the fragment component 24 by use of the cortical screws 54 and the cancellous screws 56. The greater tuberosity bone fragment 7 and the lesser tuberosity bone fragment 6 may further be secured to the humeral stem assembly 12 and the fragment component 24 by use of cables 62 and sutures 64.

Referring now to FIG. 5A, yet another embodiment of the present disclosure is shown as shoulder prosthesis 10A. The shoulder prosthesis 10A includes a humeral stem assembly 12A including a fragment component 24A that is different than the fragment component 24 of FIG. 5, in that the fragment component 24A includes screw openings 52A that include internal threads 51A which mate with external threads 53A formed in head 60A of rigid bone screws 54A. The bones screws 54A provide for a rigid construction with the fingers 32A of the fragment component 24A of the shoulder stem assembly 12A of the shoulder prosthesis 10A. The bone screws 54A as shown include threads on the shaft portion of the screws 54A that are threadably engaged with bone. Alternately the bone screws 54A may be replaced with rigid bone pegs (not shown) that are fixed in position by external threads formed in the head of the rigid bone pegs which mate with internal threads 51A in the openings 52A of fragment component 24A. The rigid bone pegs may be divergently positioned to secure the fragment component 24A to bone. The rigid bone pegs may be advantageous for use in small bone fragments.

Figure 6:
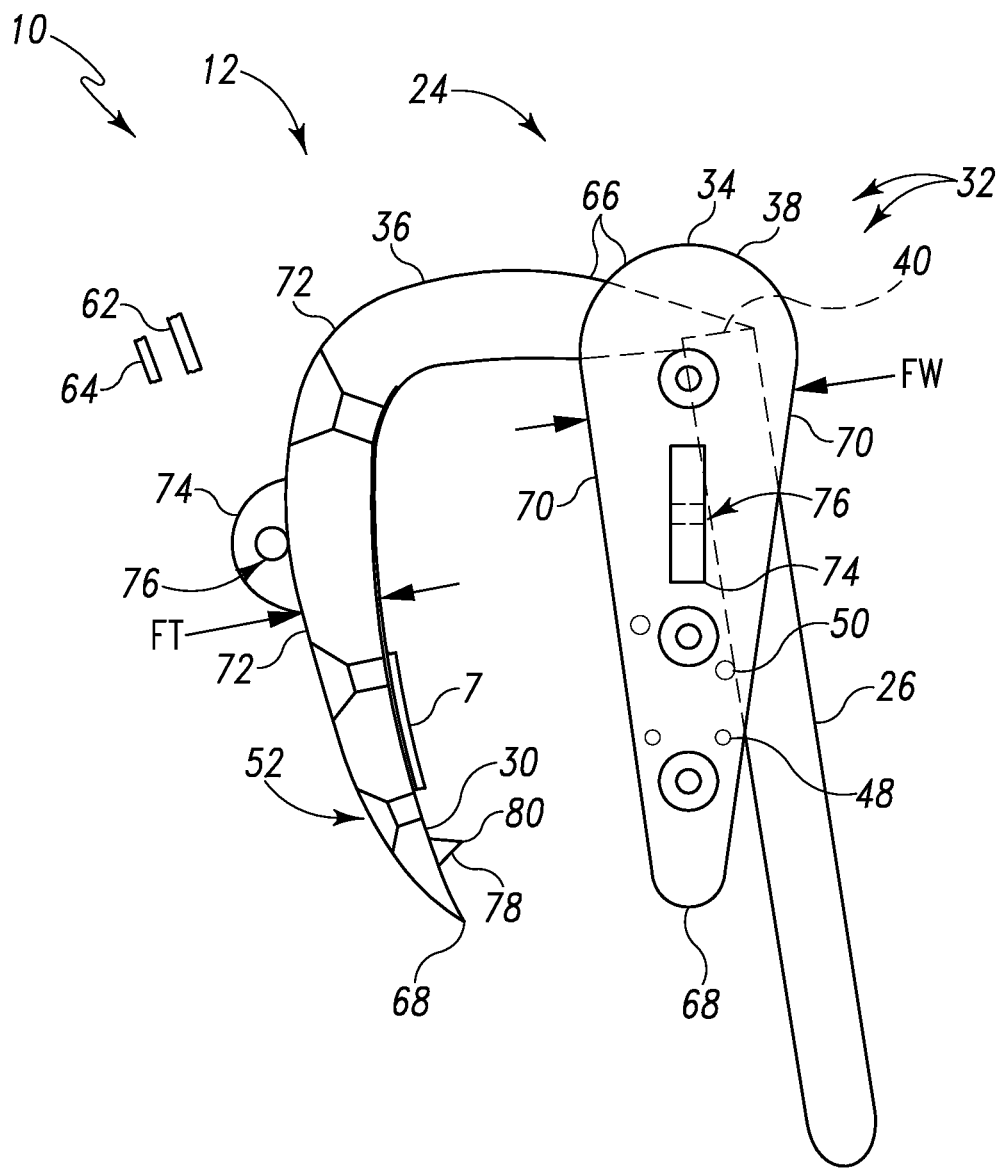
FIG. 6 is a plan view of the three fingered protrusion member of the prosthesis of FIG. 2.

Referring now to FIG. 6, the fragment component 24 is shown in greater detail. The fragment component 24 may include fingers 32 which may be a solitary finger, two fingers, or three or even more fingers. The fingers 32 are shaped and positioned to minimize irritation of soft tissue, for example, tendons, ligaments, and muscle. The fingers 32 of the fragment component 24 include a base 66 extending from end 40 of the connector 26 and a tip 68 positioned opposed to base 66. The fingers 32 may be different from each other, for example, the middle finger 36, the posterior finger 34, and the anterior finger 38 may each be different from each other. As shown in FIG. 6, the posterior finger 38 is positioned behind outer finger 34. The different shape and size of the fingers 34, 36, and 38 may be optimized for and may be dependent on the anatomical shape of the humerus 5 and, more particularly, on the shapes of the lesser tuberosity bone fragment 6 and the great tuberosity bone fragment 7.

The fingers 32 may, as is shown in FIG. 6, have common general shapes that are optimized based upon minimizing soft tissue damage and providing for the greatest strength with the minimal size of the fingers 32. For example and as shown in FIG. 6, the fingers 32 may include a finger width FW defined by the dimension between opposed sides 70 of the fingers 32. The finger width FW may decrease in dimension from base 66 to tip 68. This taper of the sides 70 may provide for less irritation to soft tissues and may provide for optimum strength of the fingers 32. The fingers 32 may further be defined by a finger thickness FT extending from contact surface 30 of the fingers 32 to exterior surface 72 of the fingers 32. The finger thickness FT may gradually decrease from base 66 to tip 68. The tapering of the finger thickness FT may minimize soft tissue irritation and provide for optimum strength of the fingers 32.

The fragment component 24 may include a protuberance 74 which may permit a transverse opening 76 to be formed in protuberance 74. The transverse opening 76 may be utilized to receive cable 62 or suture 64 as needed. Each of the fingers 34, 36, and 38 may include a solitary protuberance 74, as shown in FIG. 6, or multiple protuberances may be located on each of the fingers 32.

To secure the fingers 32 to the bone fragments 6 and 7, the fingers 32 may further include one or more spikes 78 extending inwardly from contact surface 30 of the fingers 32. The spikes 78 may have a shape that provides a point 80 for contact with the bone fragments 6 and 7. The shape may be triangular or tapered, for example the shape may be conical.

The spikes 78 may be advanced by a hammer or other suitable instrument into the bone fragments 6 and 7 to provide a rigid, proper position of the bone fragments 6 and 7.

Figures 7, 7A:
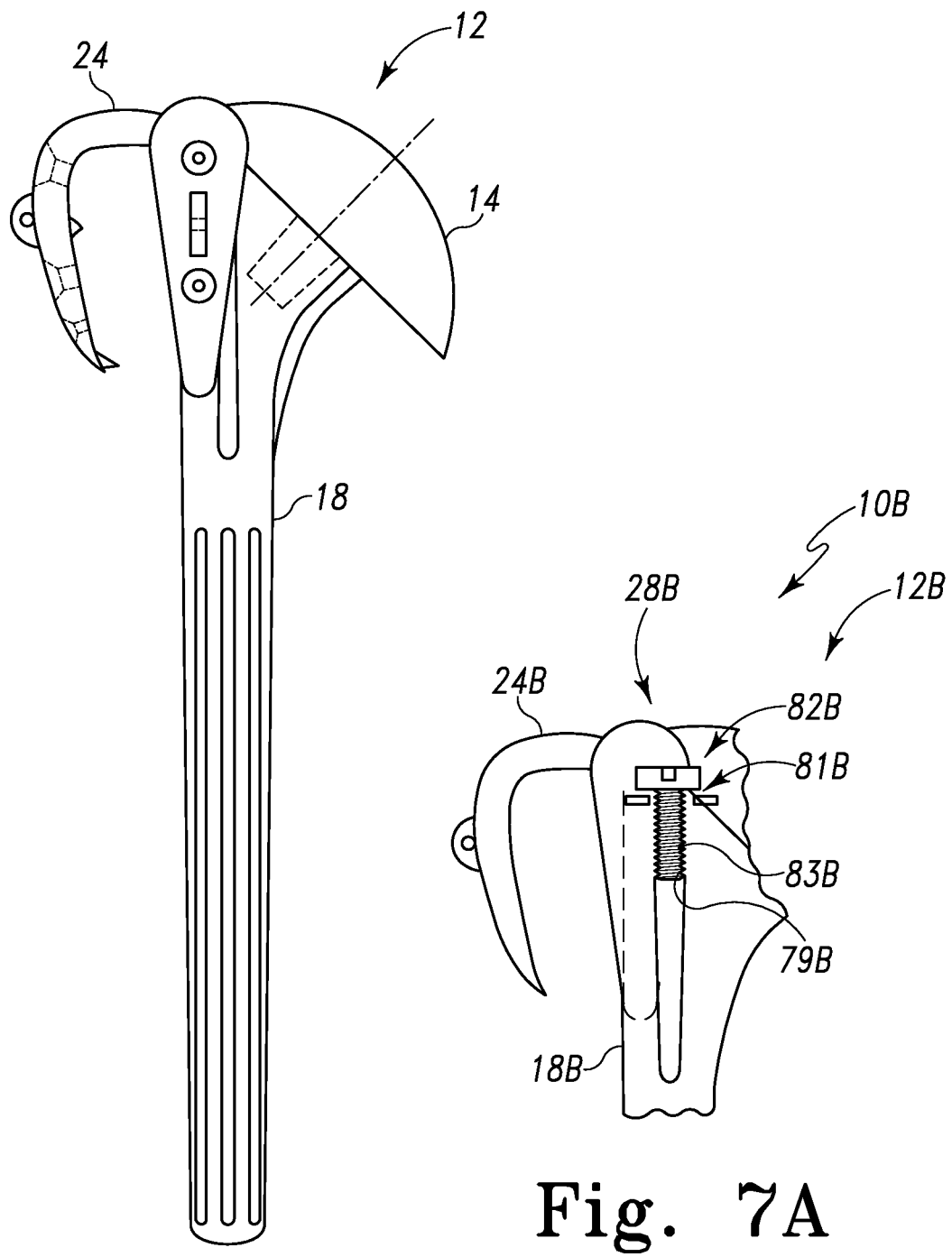
FIG. 7 is a plan view of the prosthesis of FIG. 2.
FIG. 7A is a partial plan view partially in cross section of a fragment member with a fastener to secure the fragment member to the stem according to another embodiment of the present disclosure.
Figure 8:
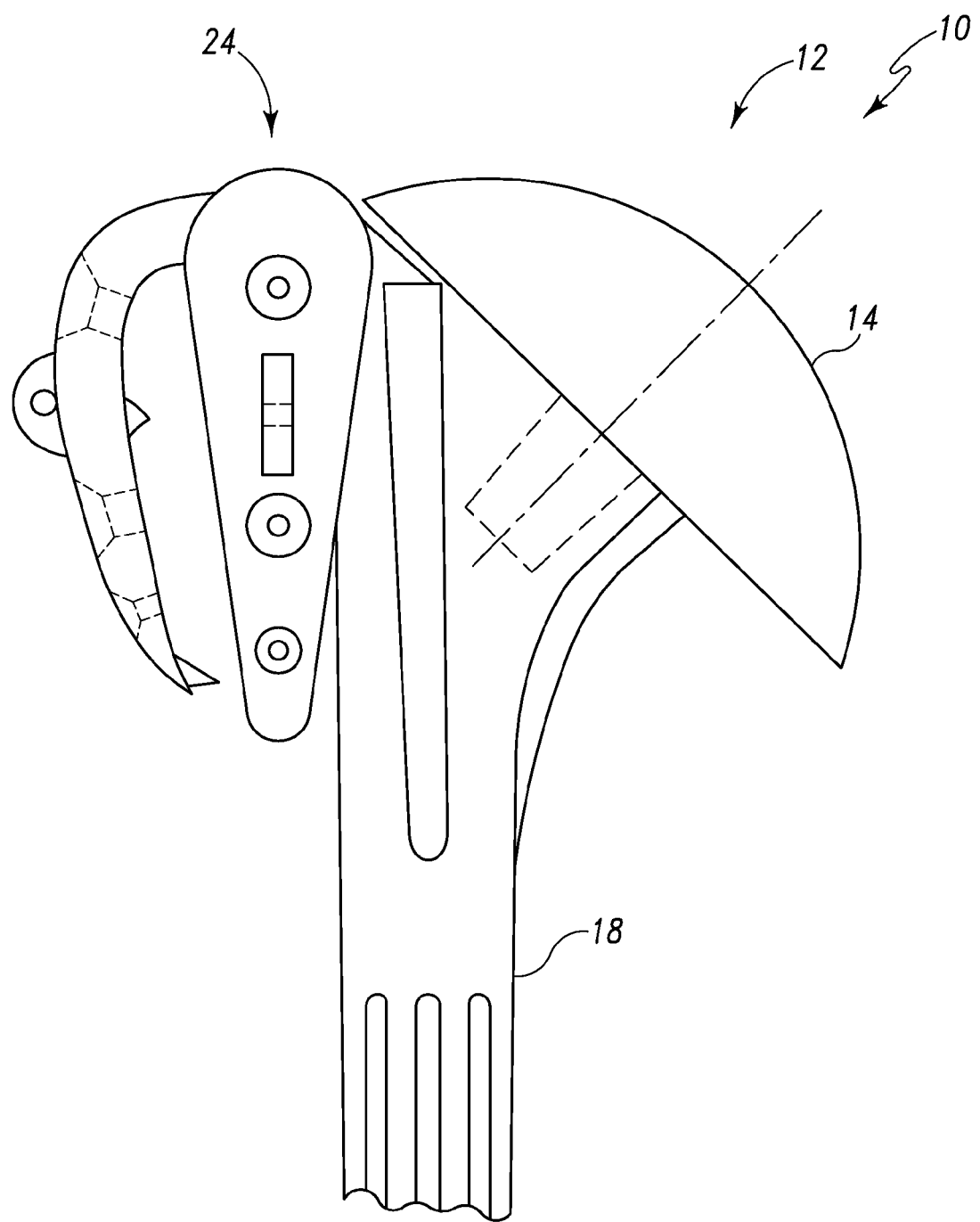
FIG. 8 is a partial plan view of the prosthesis of FIG. 2 showing the area around the protrusion member in greater detail.
Figure 9:
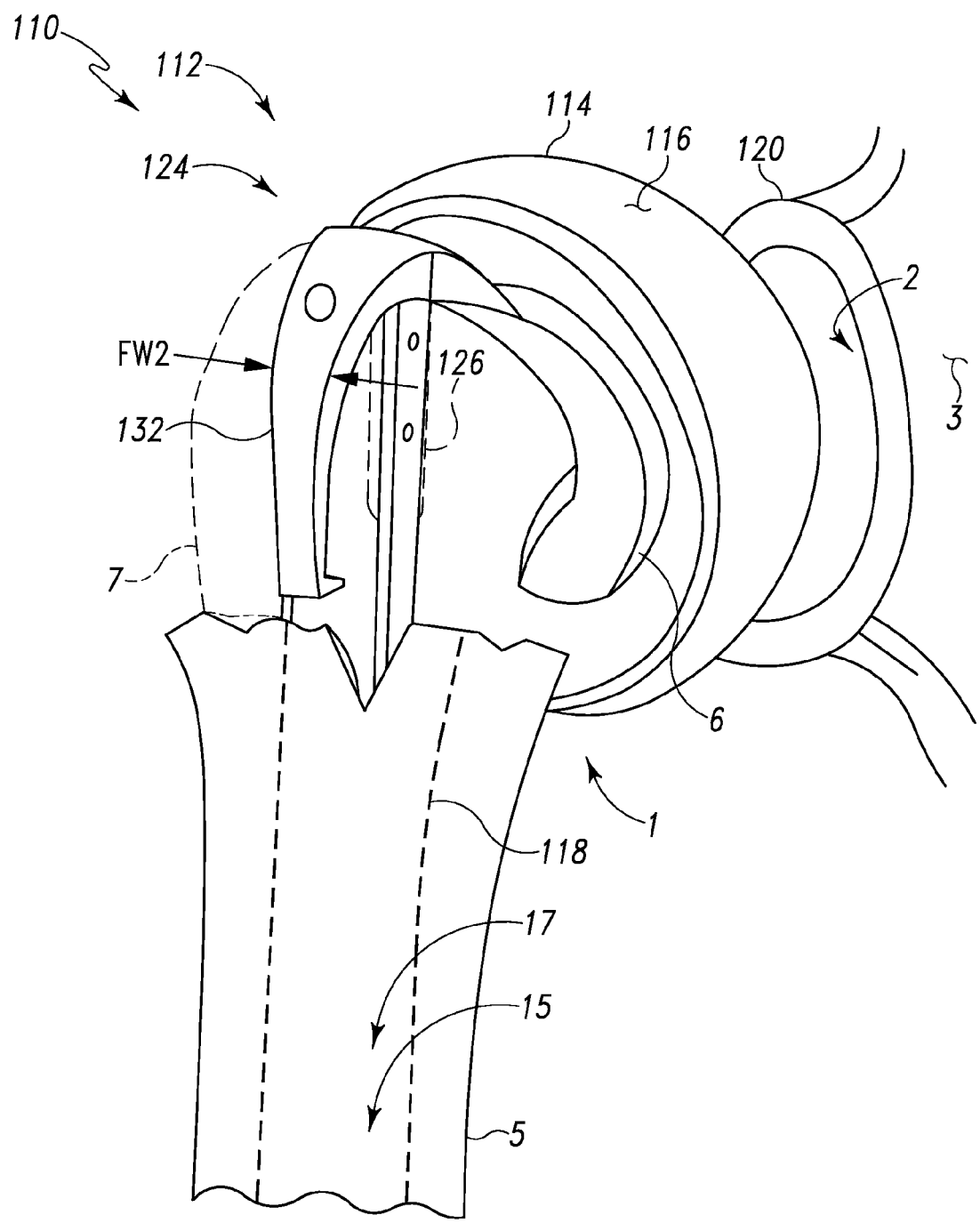
FIG. 9 is a perspective view of a prosthesis with a single fingered protrusion member according to another embodiment of the present disclosure in position in a humerus with a humeral fracture.

Referring now to FIGS. 7 and 8, the assembled shoulder stem assembly 12 is shown. The shoulder stem assembly 12 includes the stem portion or stem component 18 to which head component 14 and fragment component 24 are secured.

Referring now to FIG. 7A, yet another embodiment of the present disclosure is shown as shoulder prosthesis 10B. The shoulder prosthesis 10B includes a shoulder stem assembly 12B that is somewhat different than the shoulder stem assembly of FIGS. 2-7 in that the shoulder stem assembly 12B includes a fragment component 24B that is secured to a stem component 18B in an alternate manner. As shown in FIG. 7A, a fastener in the form of, for example, screw 82B is positioned through opening 81B in the fragment component 24B. The screw 82B includes external threads 83B which are fitted to internal threads 79B formed in opening 28B of the stem component 18B. The screw 82B, rather than a tapered protrusion, is used to secure the fragment component 24B to the stem component 18B of the stem assembly 12B of the prosthesis 10B.

According to the present disclosure and referring to FIGS. 9-13, yet another embodiment of the present disclosure is shown as prosthesis 110. The prosthesis 110 includes a shoulder stem assembly 112 which cooperates with a glenoid component 120. The glenoid component 120 is secured to glenoid cavity 2 of the scapula 3. The shoulder stem assembly 112 includes a stem component 118 which is similar to the stem component 18 of FIGS. 2-8 and is fitted into cavity 17 of intramedullary canal 15 of the humerus 5. The shoulder stem assembly 112 further includes a head component 114 which is similar to the head component 14 of the prosthesis 10 of FIGS. 2-8. The head component 114 is removeably secured to stem component 118. The head component 114 includes an articulating surface 116 that articulates with glenoid component 120.

The prosthesis 110 further includes fragment component 124 which is a part of the shoulder stem assembly 112. The fragment component 124 is different than the fragment component 24 of the prosthesis 10 of FIGS. 2-8 in that fragment component 124 includes a single or solitary finger 132. The finger 132 has a finger width FW2 which is selected to support or connect with both lesser tuberosity fragment 6 and greater tuberosity fragment 7. The width FW2 of the finger 132 may be significantly wider than the finger width FW of the fingers 32 of the fragment component 24 of the prosthesis 10 of FIGS. 2-8.

Figure 10:
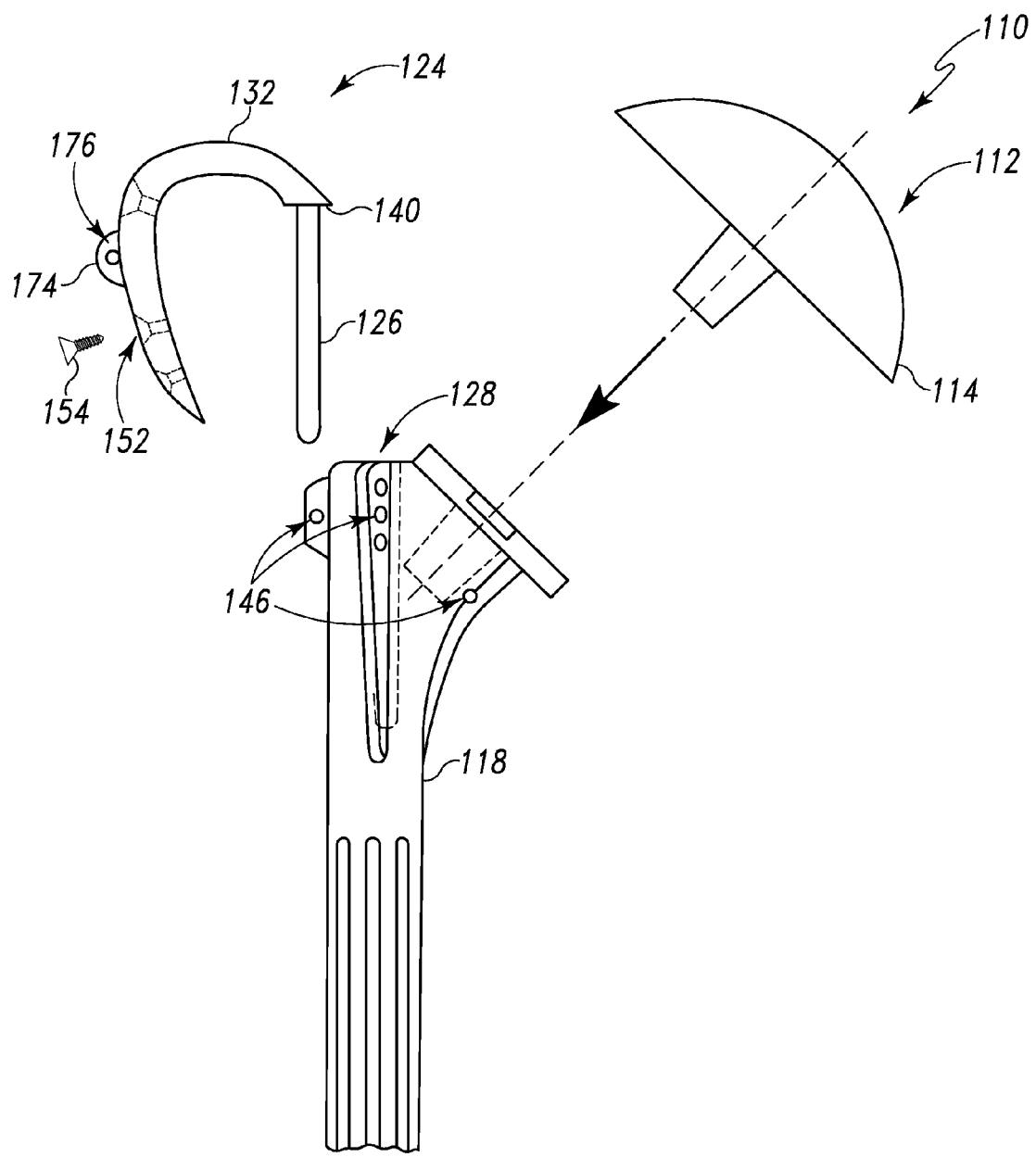
FIG. 10 is an exploded plan view of the prosthesis of FIG. 9.

Referring now to FIG. 10, the shoulder stem assembly 112 of the prosthesis 110 is shown in a disassembled condition. The head component 114 is removeably connected to stem component 118. The stem component 118 may include holes 146 for receiving sutures. The stem assembly 112 further includes the fragment component 124. The fragment component 124 includes a connector 126 that fits into longitudinal opening 128 formed in stem component 118. The fragment component 124 includes a finger 132 that extends from proximal end 140 of the connector 126. The finger 132 may include, for example, a screw opening or a plurality of screw openings 152 for receiving screws 154 for securing the fragment component 124 to lesser tuberosity fragment 6 and greater tuberosity fragment 7. The finger 132 may, as shown in FIG. 10, include a protuberance 174 in which transverse opening 176 is formed.

Figure 11:
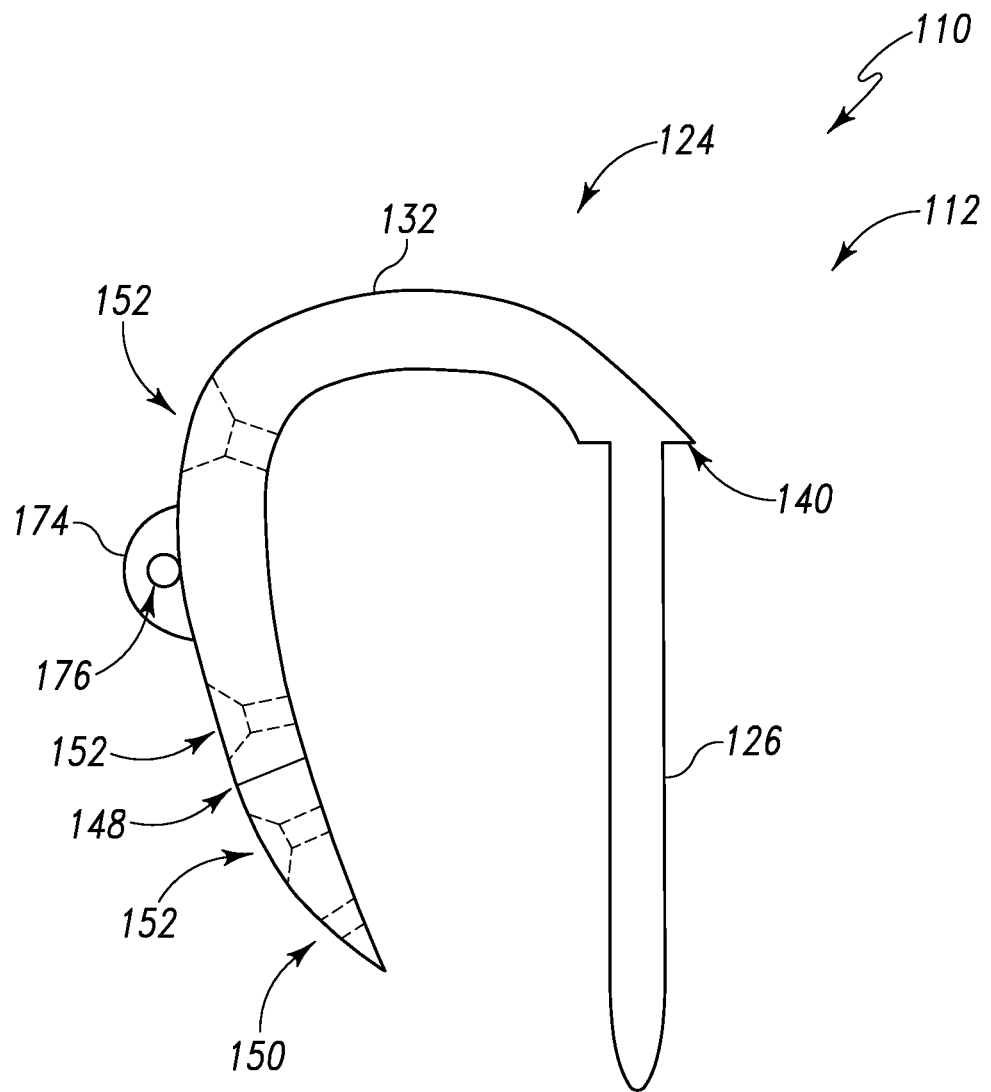
FIG. 11 is a plan view of the single fingered protrusion member of the prosthesis of FIG. 9.

Referring now to FIG. 11, the fragment component 124 of the shoulder stem assembly 112 of the prosthesis 110 is shown in greater detail. The fragment component 124 includes the finger 132 that extends from proximal end 140 of the connector 126. The finger 132 includes the screw openings 152 as well as transverse opening 176 formed in protuberance 174. The finger 132 may further include one or more cable openings 150 and suture openings 148.

Figure 12:
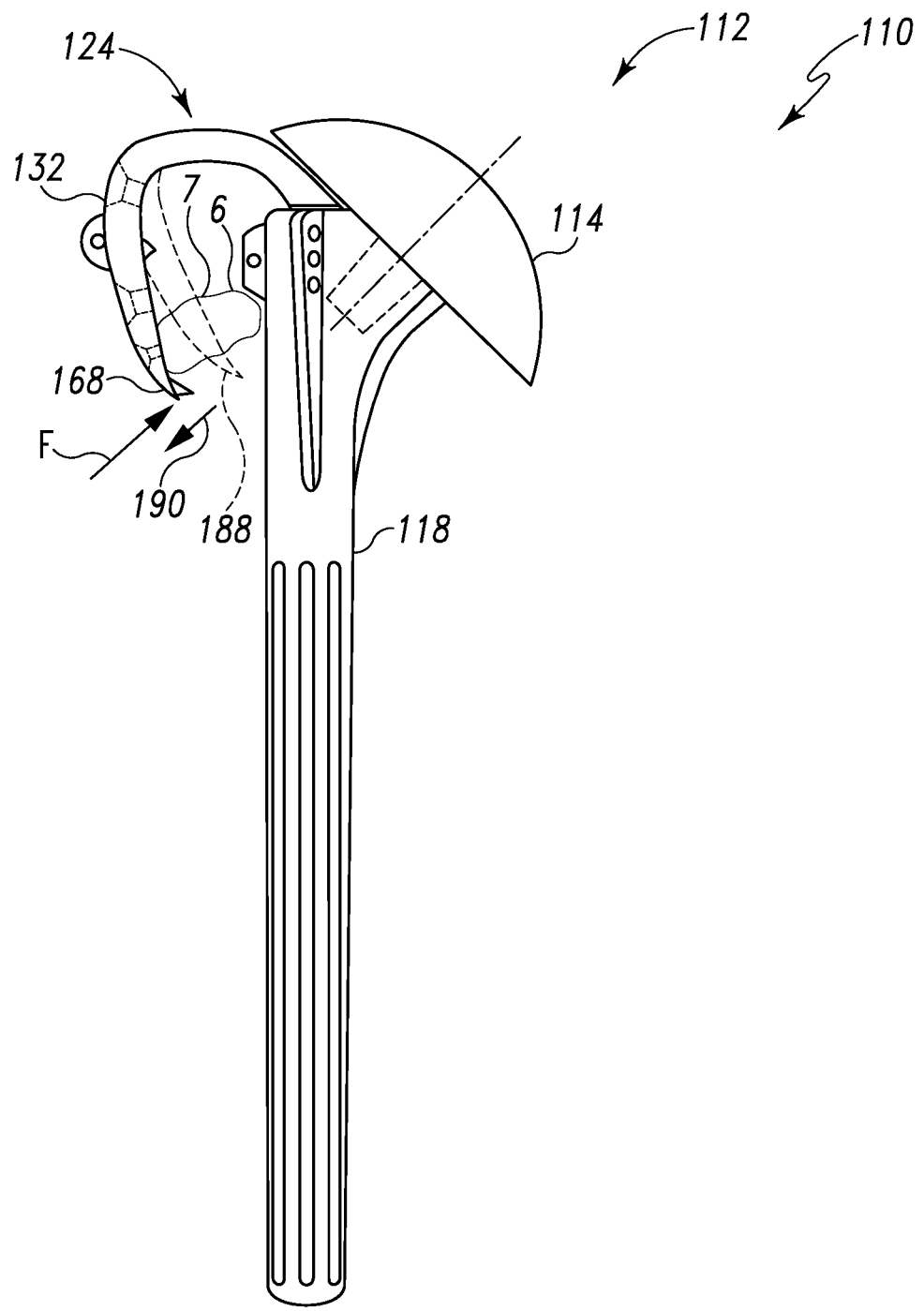
FIG. 12 is a plan view of the prosthesis of FIG. 9.

Referring now to FIG. 12, the fragment component 124 is shown assembled to the stem component 118 and the head 114 is shown assembled onto the stem component 118 to form the shoulder stem assembly 112. The fragment component 124 may be made of, for example, a resilient material, for example, titanium. The fragment component 124 may have a natural position 188, as shown in phantom, in which tip 168 of the finger 132 is considerably closer to the stem component 118 of the stem assembly 112. When the fragment component 124 is positioned in the body, the finger 132 of the fragment component 124 is urged in the direction of arrow 190 such that a compression or reduction force F is placed upon the bone fragments 6 and 7 to urge them into reduction to promote a union of the fracture and proper healing of the fracture site.

Figure 13:
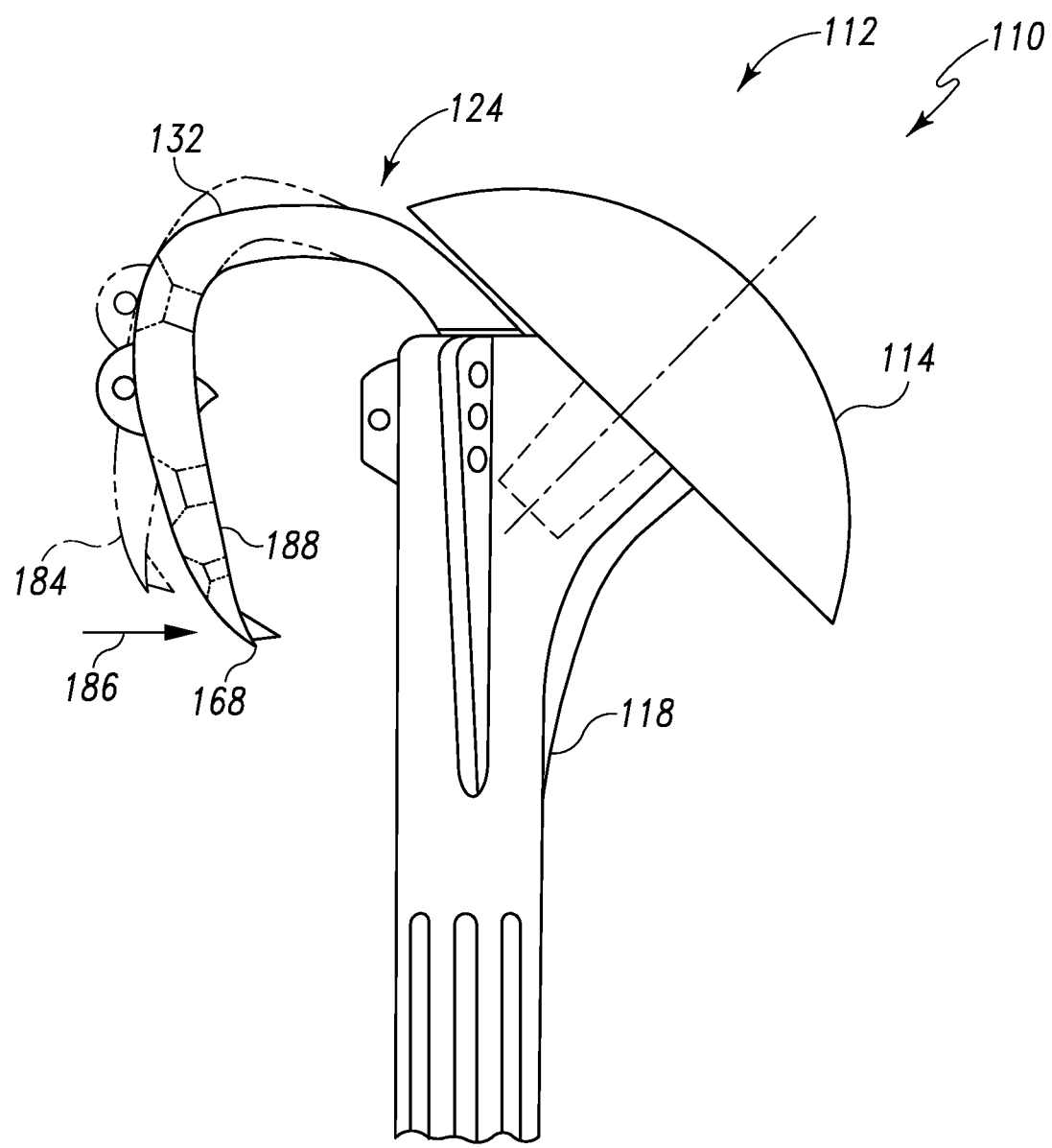
FIG. 13 is a partial plan view of the prosthesis of FIG. 9 showing the area around the protrusion member in greater detail.

Referring now to FIG. 13, the fragment component 124 of the shoulder stem assembly 112 of the prosthesis 110 is shown with the fragment component 124 made of, for example, a memory metal component, such as nitinol. The fragment component 124 includes a cold position 184, as shown in phantom, in which the fragment component 124 is put, for example, in a freezer of subjected to temperature substantially below ambient such that the fragment component 124 forms the shape of cold position 184. The fragment component 124 may, for example, be kept on ice in the surgery room until immediately prior to insertion into the body. Once subjected to ambient or the patient's internal body temperature, the fragment component 124 may move in the direction of arrow 186 to implant or in situ position 188, as shown in solid. By having the fragment component 124 have its finger 132 moved in the direction of arrow 186 from the cold position 184 to the assembled, natural position 188, the bone fragments 6 and 7 may be urged into position against each other and the humerus such that reduction and union at the joint is facilitated.

It should be appreciated that both with the use of a resilient component, for example a titanium fragment component and/or with the use of a fragment component made of a memory metal, urging of the fragment component against the bone fragments 6 and 7 may be accomplished in any of the embodiments of the present disclosure. The embodiment shown in FIGS. 12 and 13 is shown illustratively for simplicity with a solitary finger. If such resilient materials are used, typically each finger is made of such resilient materials and each finger moves to urge the bone fragments into the reduced state. Such urging of the fragments into a reduced state is preferred, but not required, for the embodiments of the present disclosure.

Figure 14:
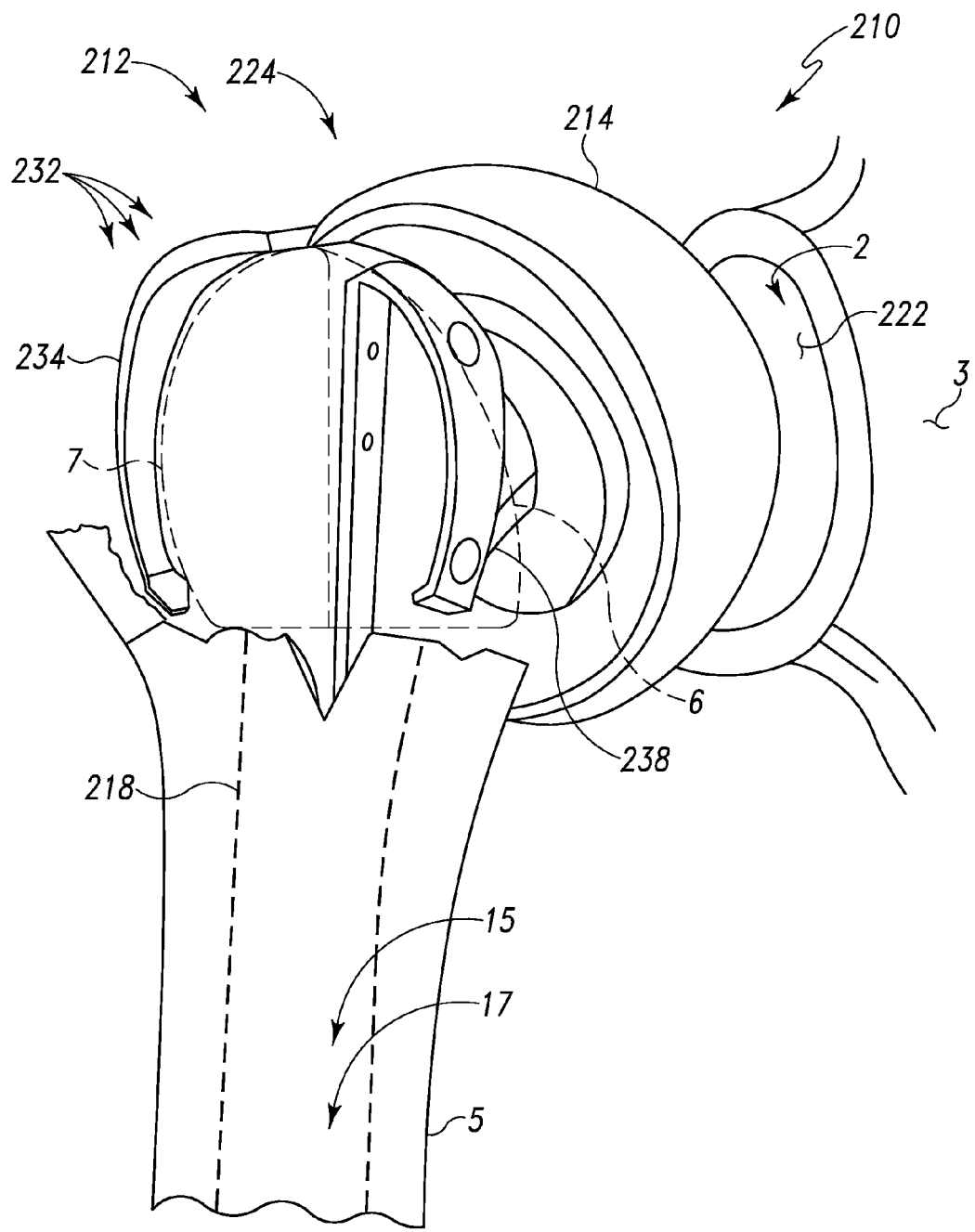
FIG. 14 is a perspective view of a prosthesis with a two fingered protrusion according to yet another embodiment of the present disclosure in position in a humerus with a humeral fracture.
Figure 15:
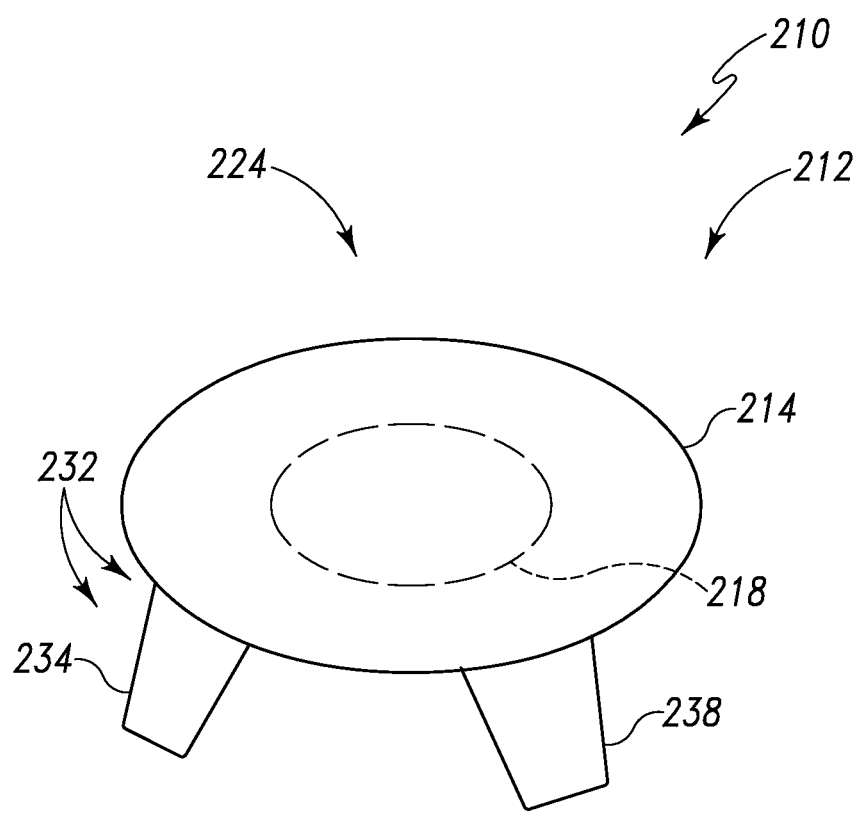
FIG. 15 is an top view of the prosthesis of FIG. 14.

According to the present disclosure and referring now to FIGS. 14 and 15, yet another embodiment of the present disclosure is shown as prosthesis 210. The prosthesis 210 includes a stem assembly 212 that articulatingly cooperates with glenoid component 222 secured to glenoid cavity 2 of scapula 3. The stem assembly 212 includes a stem component 218 similar to the stem component 18 of FIGS. 2-8. The stem component 218 is received, as least partially, in cavity 17 formed in intramedullary canal 15 of the humerus 5. The stem assembly 212 further includes a head component 214 which is removeably secured to component 218. The stem assembly 212 further includes a fragment component 224 which is different than the fragment component 24 of the stem assembly 12 of FIGS. 2-8 in that the fragment component 224 includes two spaced apart fingers 232 rather than the three fingers of the fragment component 24 of FIGS. 2-8. The fragment component 224 includes a posterior finger 234 to which greater tuberosity fragment 7 is secured and an anterior finger 238 to which lesser tuberosity fragment 6 is secured.

Figure 16:
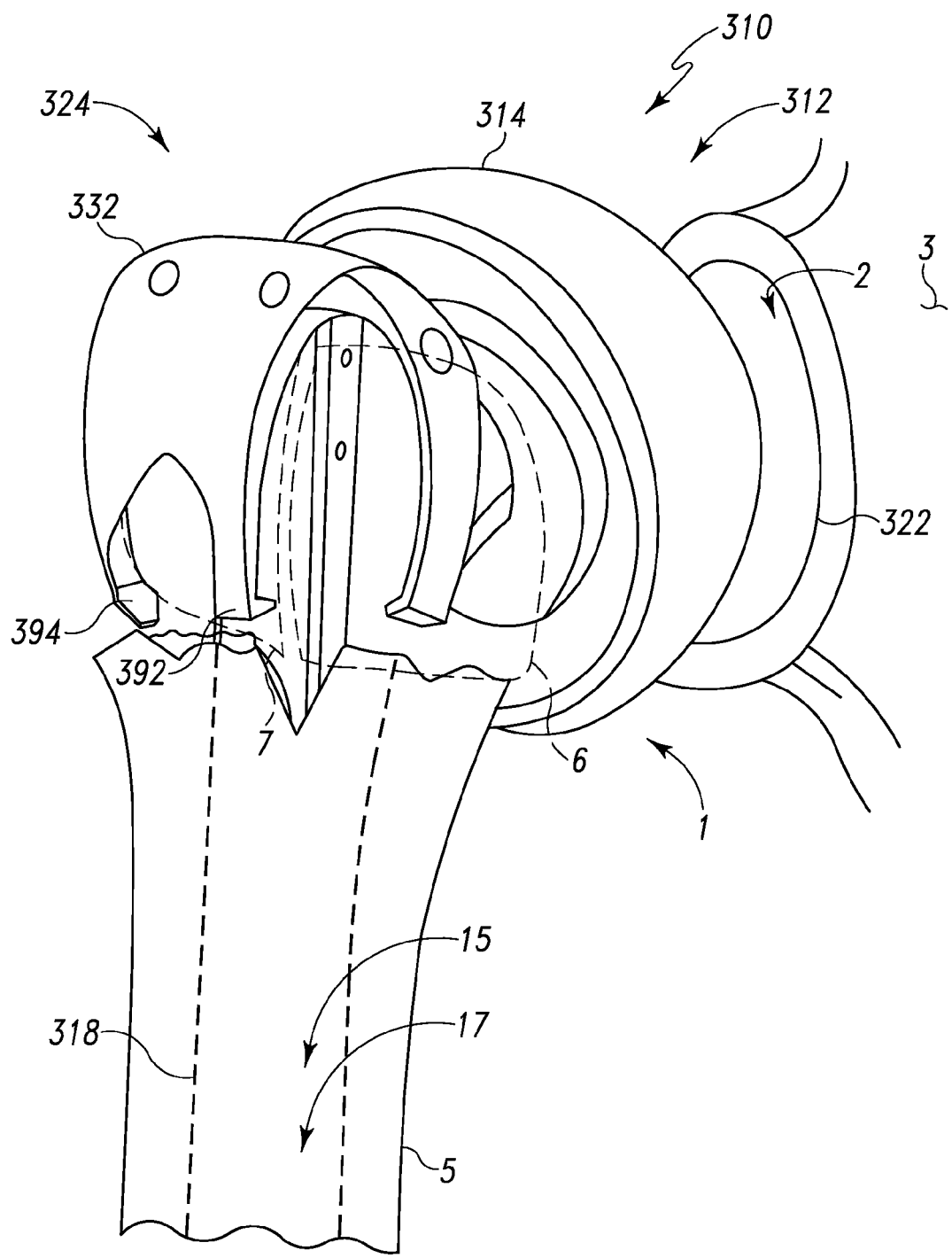
FIG. 16 is a perspective view of a prosthesis with a two fingered protrusion with a forked finger according to yet another embodiment of the present disclosure in position in a humerus with a humeral fracture.
Figure 17:
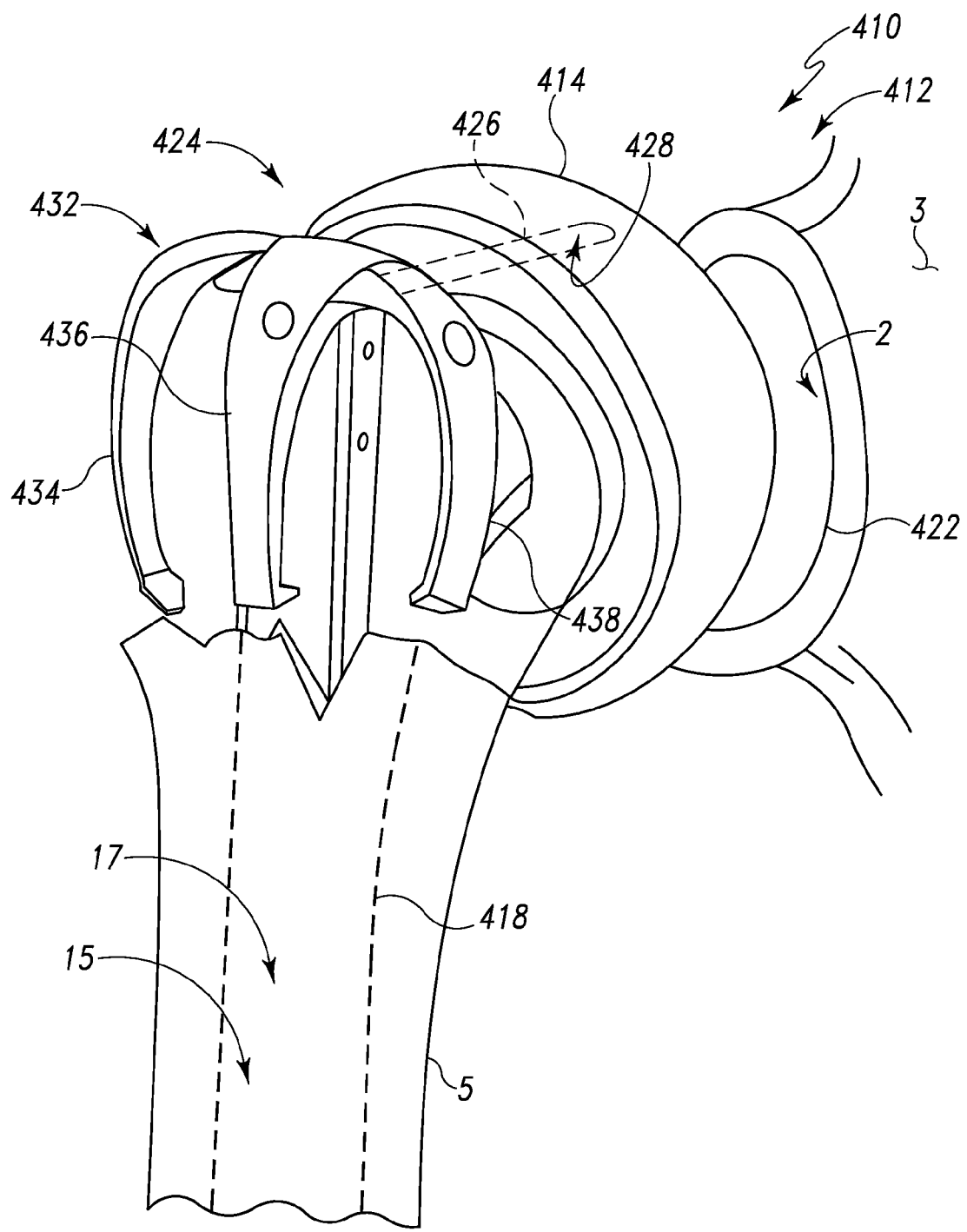
FIG. 17 is a perspective view of a prosthesis with a three fingered protrusion with an alternate construction according to yet another embodiment of the present disclosure in position in a humerus with a humeral fracture.

Referring now to FIG. 16, yet another embodiment of the present disclosure is shown as prosthesis 310. The prosthesis 310 includes a stem assembly 312 which cooperates with glenoid component 322. The glenoid component 322 is secured to glenoid cavity 2 of scapula 3. The stem assembly 312 includes a stem component 318 which is secured, at least partially, in cavity 17 formed in canal 15 of the humerus 5. A head component 314 is removeably secured to the stem component 318. The stem assembly 312 further includes a fragment component 324 which is different than the fragment component 24 of the prosthesis 10 of FIGS. 2-8 in that the fragment component 324 includes a solitary finger 332 that has an anterior fork 392 and posterior fork 394. The anterior fork 392 is adapted to contain lesser tuberosity fragment 6 while the posterior fork 394 is adapted to secure greater tuberosity fragment 7.

According to the present disclosure and referring now to FIGS. 17-22, yet another embodiment of the present disclosure is shown as prosthesis 410. The prosthesis 410 of FIGS. 17-22 includes a stem assembly 412 which is in articulating cooperation with glenoid component 422. The glenoid component 422 is secured to glenoid cavity 2 of scapula 3

The stem assembly 412 includes a stem component 418 which is fitted into cavity 17 formed in canal 15 of humerus 5. The stem component 418 is similar to the stem component 18 of FIGS. 2-8. The stem component 418, however, does not include the longitudinal opening 28 of the stem component 18. The stem assembly 412 further includes a head component 414 which is removeably secured to stem component 418. The head component 414 is similar to the head component 14 of the stem assembly 12 of FIGS. 2-8 except that the head component 414 includes an opening 428 for cooperation with fragment component 424.

The stem assembly 412 further includes fragment component 424 which is similar to the fragment component 24 of the prosthesis 10 of FIGS. 2-8 except that the fragment component 424 is secured to head component 414 and not to stem component 418. Fragment component 424 includes a connector 426 which is removeably secured to opening 428 formed in the head component 414. The fragment component 424 includes a finger or fingers, for example an anterior finger 438, a middle finger 436, and a posterior finger 434. The fingers 434, 436, and 438 are similar to the fingers 34, 36, and 38 of the fragment component 24 of the prosthesis 10 of FIGS. 2-8.

The stem assembly 412 further includes fragment component 424 which is similar to the fragment component 24 of the prosthesis 10 of FIGS. 2-8 except that the fragment component 424 is secured to head component 414 and not to stem component 418. Fragment component 424 includes a connector 426 which is removeably secured to opening 428 formed in the head component 414. The fragment component 424 includes a finger or fingers, for example an anterior finger 438, a middle finger 436, and a posterior finger 434. The fingers 434, 436, and 438 are similar to the fingers 34, 36, and 38 of the fragment component 24 of the prosthesis 10 of FIGS. 2-8.

Figures 18, 19:
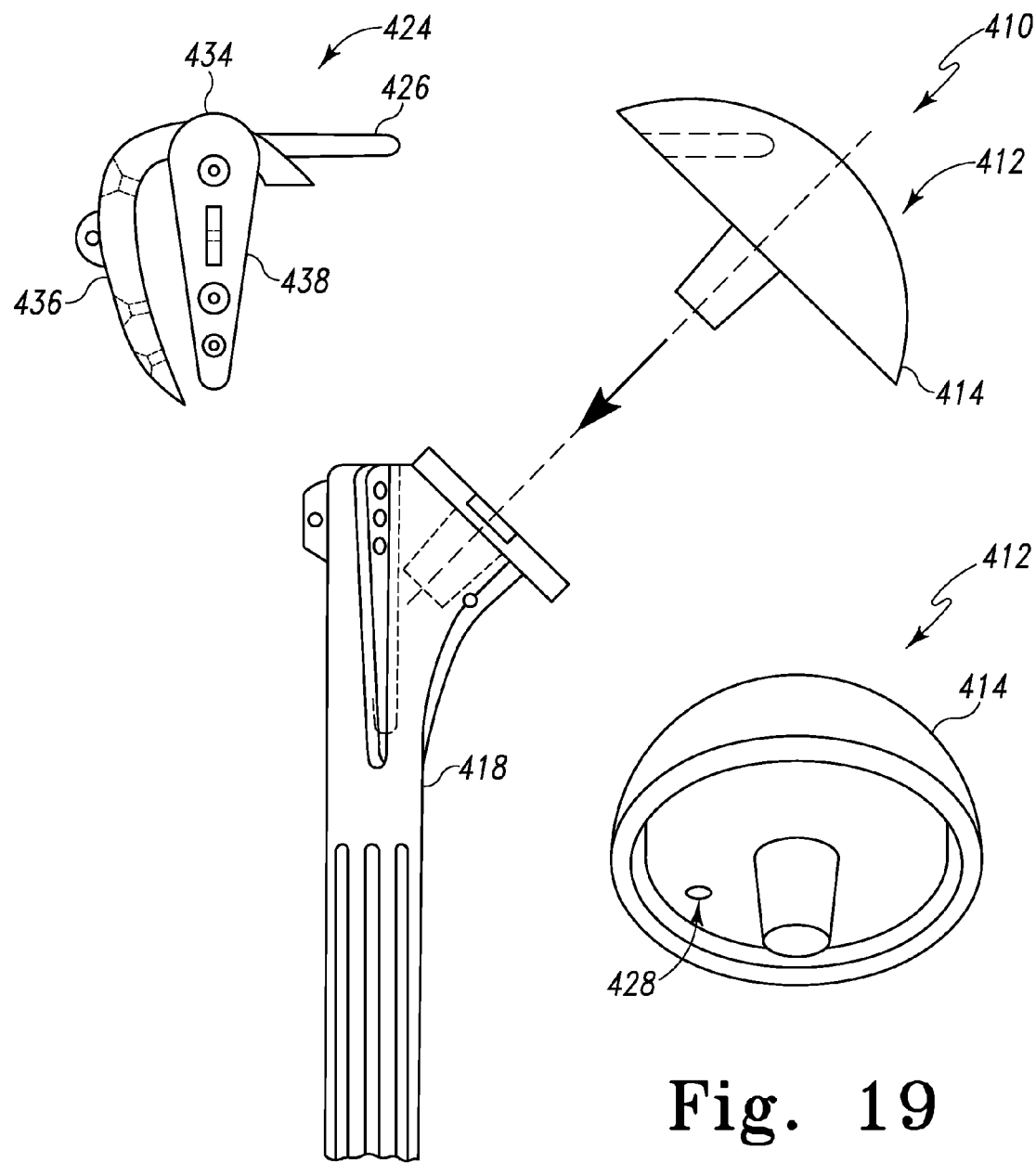
FIG. 18 is an exploded plan view of the prosthesis of FIG. 17.
FIG. 19 is a perspective view of a head with an opening for receiving a stem of the protrusion member of the prosthesis of FIG. 17.

Referring now to FIG. 18, the stem assembly 412 of the prosthesis 410 is shown in an unassembled condition. The stem assembly 412 includes head component 414 which is removeably secured to stem component 418. The stem assembly 412 further includes a fragment component 424 which is removeably secured to head component 414 by connector 426 which is fittingly received into opening 428 in the head component 414. The fragment component 424 includes anterior finger 438, middle finger 436, and posterior finger 434.

Referring now to FIG. 19, the opening 428 is shown in head component 414.

Figure 20:
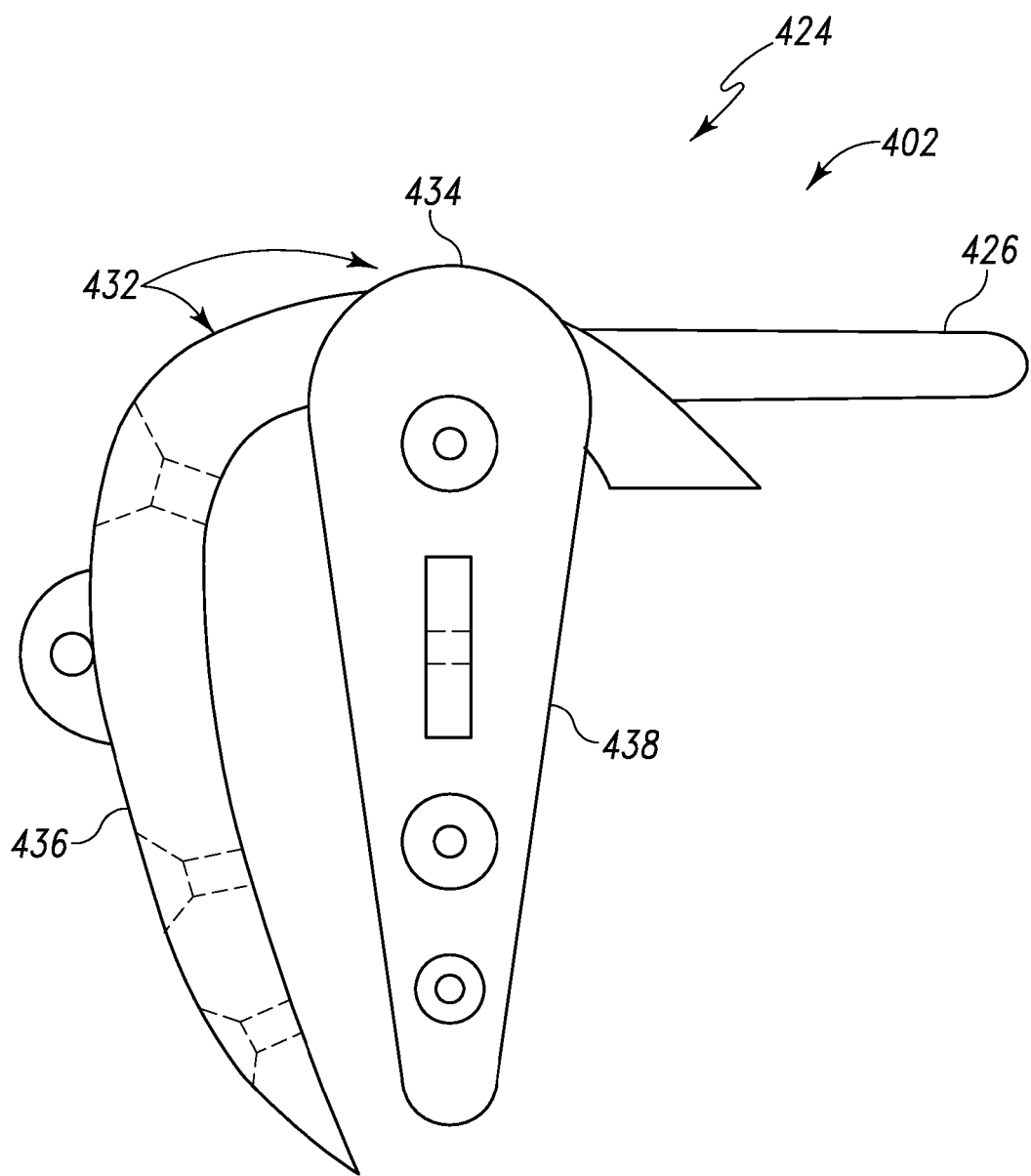
FIG. 20 is a plan view of the protrusion member of the prosthesis of FIG. 14.

Referring now to FIG. 20, the fragment component 424 is shown in greater detail. The fragment component 424 includes posterior fork 434, middle fork 436, and anterior fork 438. The forks 432 are fitted to connector 426 which is used to secure the fragment component 424 to the head component 414.

Figure 21:
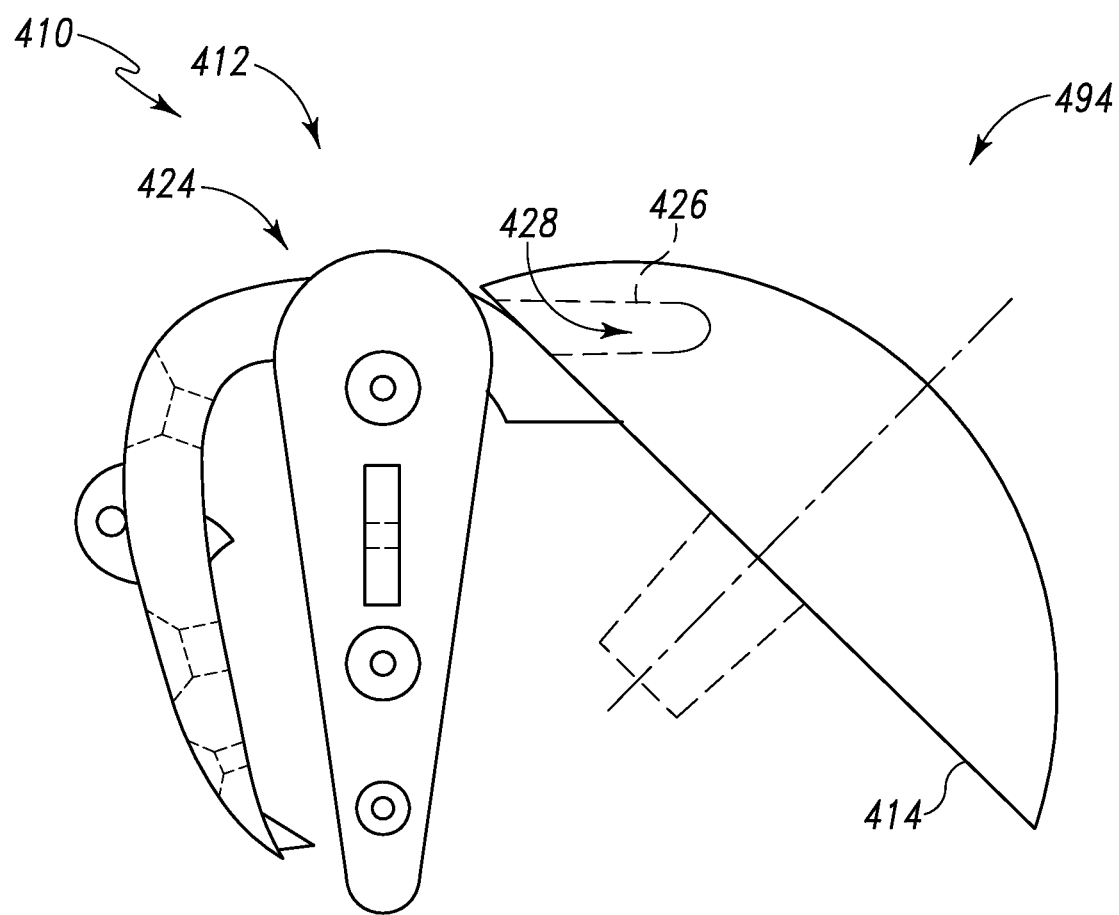
FIG. 21 is a plan view of an assembly of the head of FIG. 19 with the protrusion member of FIG. 20.

Referring now to FIG. 21, a head fragment assembly 494 is shown. The head fragment assembly 494 includes fragment component 424. The fragment component 424 includes connector 426. The head fragment assembly 494 also includes head component 414 that includes opening 428 for receiving the connector 426 of the fragment component 424.

Figure 22:
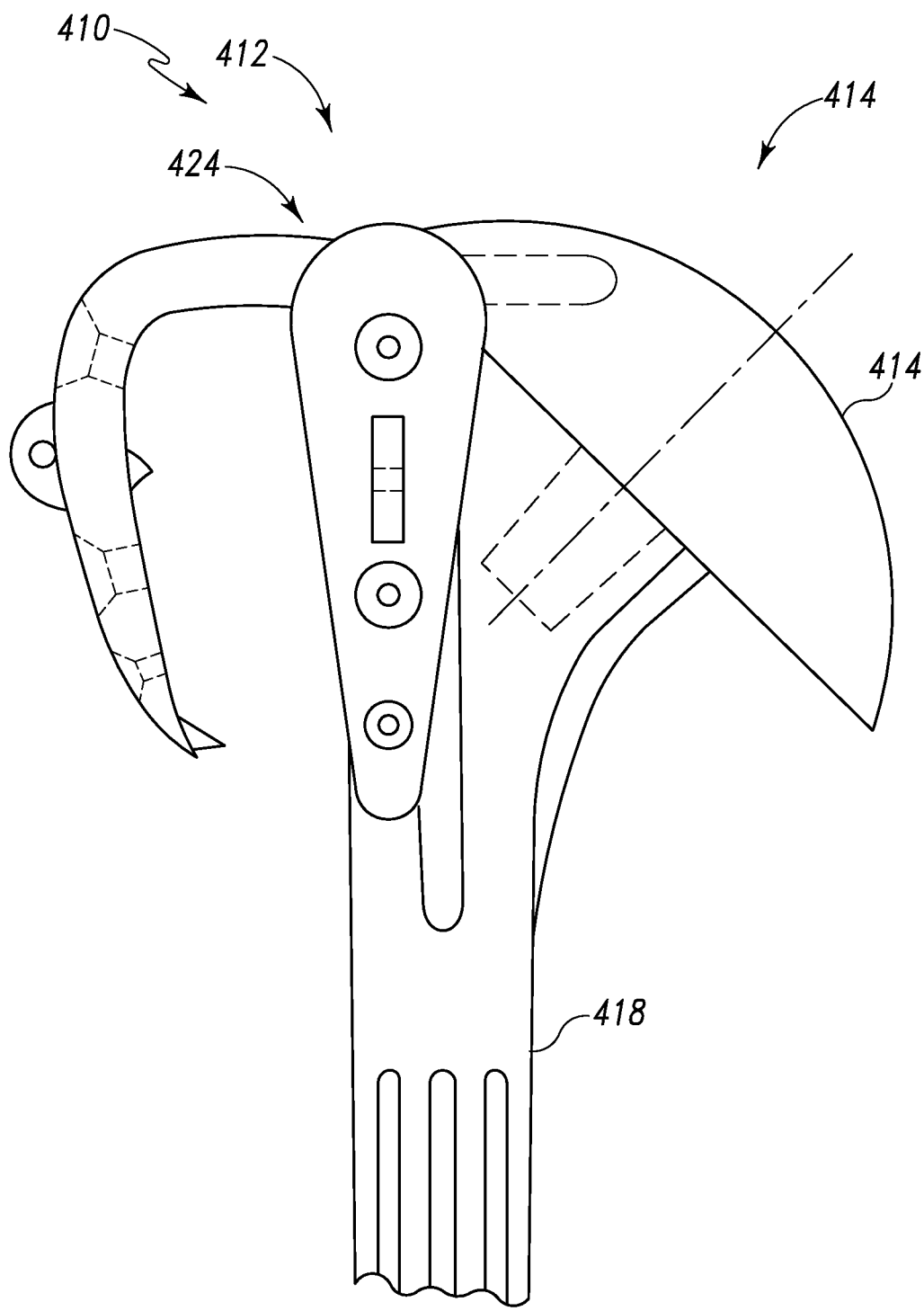
FIG. 22 is a partial plan view of the prosthesis of FIG. 19 showing the area around the protrusion member in greater detail.
Figure 23:
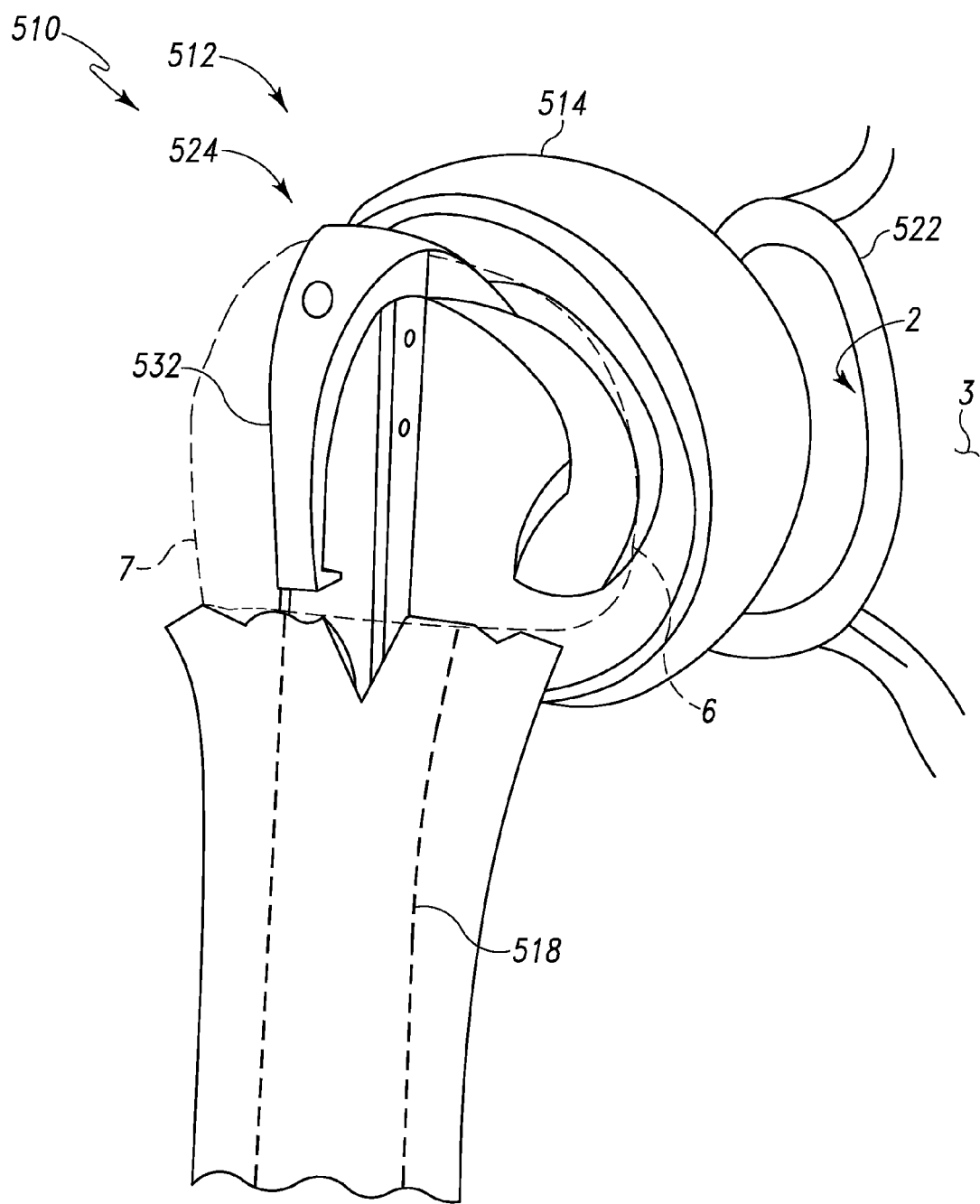
FIG. 23 is a perspective view of a prosthesis with a single fingered protrusion with an alternate construction according to yet another embodiment of the present disclosure in position in a humerus with a humeral fracture.

Referring now to FIG. 22, the head fragment assembly 494 is shown assembled to stem component 418 to form the stem assembly 412 of the prosthesis 410.

Referring now to FIGS. 23-27, yet another embodiment of the present disclosure is shown as prosthesis 510. The prosthesis 510 is similar to the prosthesis 410 of FIGS. 17-22 except that the prosthesis 510 includes a fragment component 524 with a solitary finger 532. The prosthesis 510 includes a stem assembly 512 which is in articulating cooperation with glenoid component 522. The glenoid component 522 is secured to glenoid cavity 2 of scapula 3. The stem assembly 512 includes a stem component 518 similar to the stem component 418 of the prosthesis 410 of FIGS. 17-22.

The stem assembly 512 further includes a head component 514 which removeably secured to stem component 518. The head component 514 is similar to the head component 414 of the prosthesis 410 of FIGS. 17-22. The stem assembly 512 further includes a fragment component 524 that is somewhat different than the fragment component 424 of the stem assembly 412 of FIGS. 17-22 in that the fragment component 524 includes a solitary finger 532. The solitary finger 532 may be sufficiently wide to support or constrain both lesser tuberosity bone fragment 6 and greater tuberosity bone fragment 7.

Figure 24:
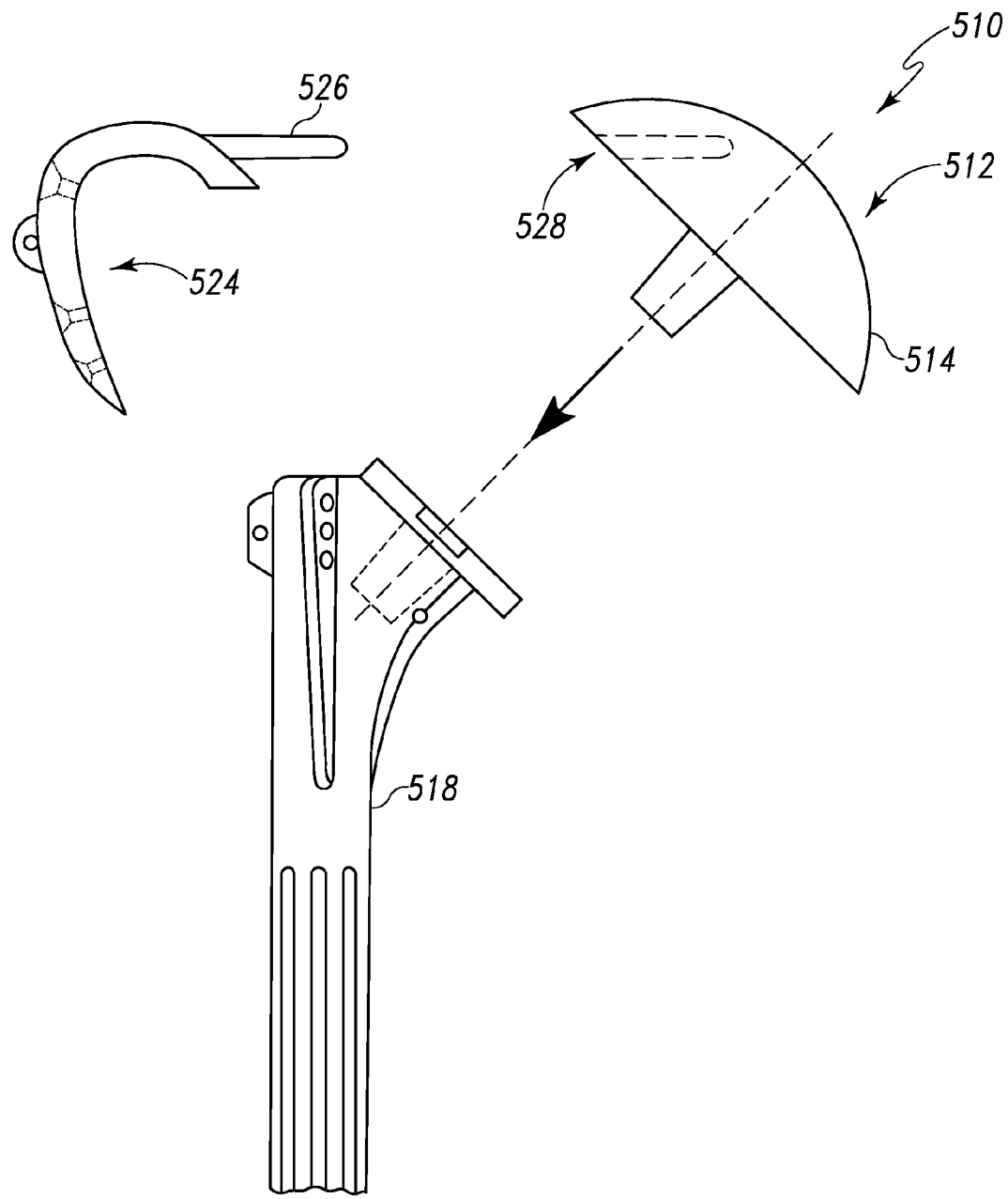
FIG. 24 is an exploded plan view of the prosthesis of FIG. 23.

Referring now to FIG. 24, the stem assembly 524 of the prosthesis 510 is shown in an exploded view. The head component 514 is removeably secured to stem component 518. The fragment component 524 is removeably secured to head component 514 by connector 526 extending from the fragment component 524. The connector 526 fits into opening 528 formed in head component 514.

Figure 25:
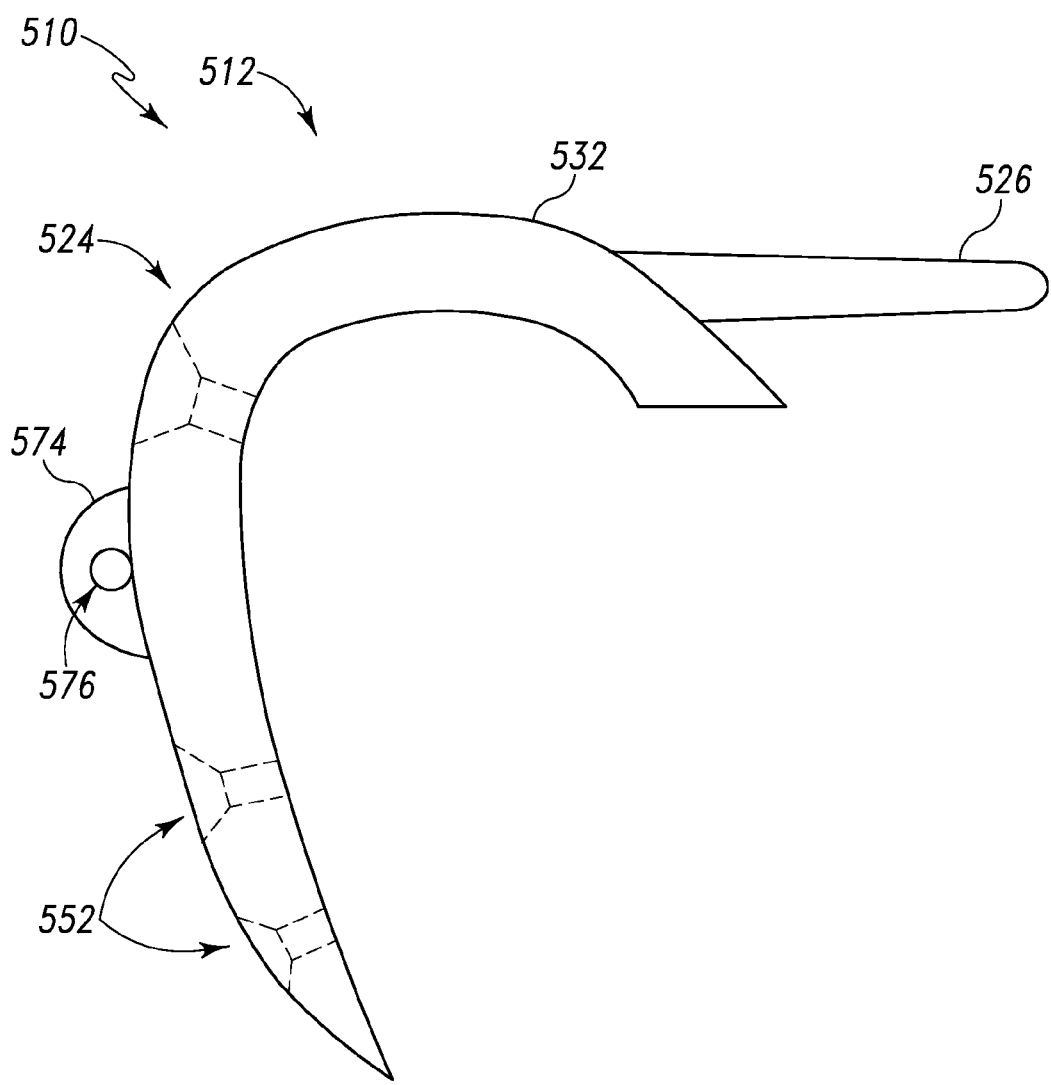
FIG. 25 is a plan view of the protrusion member of the prosthesis of FIG. 23.

Referring now to FIG. 25, the fragment component 524 is shown in greater detail. The fragment component 524 includes a connector 526 as well as finger 532 extending from the connector 526. The finger 532 may include a plurality of screw openings 552 as well as a protuberance 574 which defines a transverse opening 576. The transverse opening 576 may be utilized with cables or sutures and the screw openings 552 may be utilized for receiving screws to secure fragments 6 and 7 to the fragment component 524.

Figure 26:
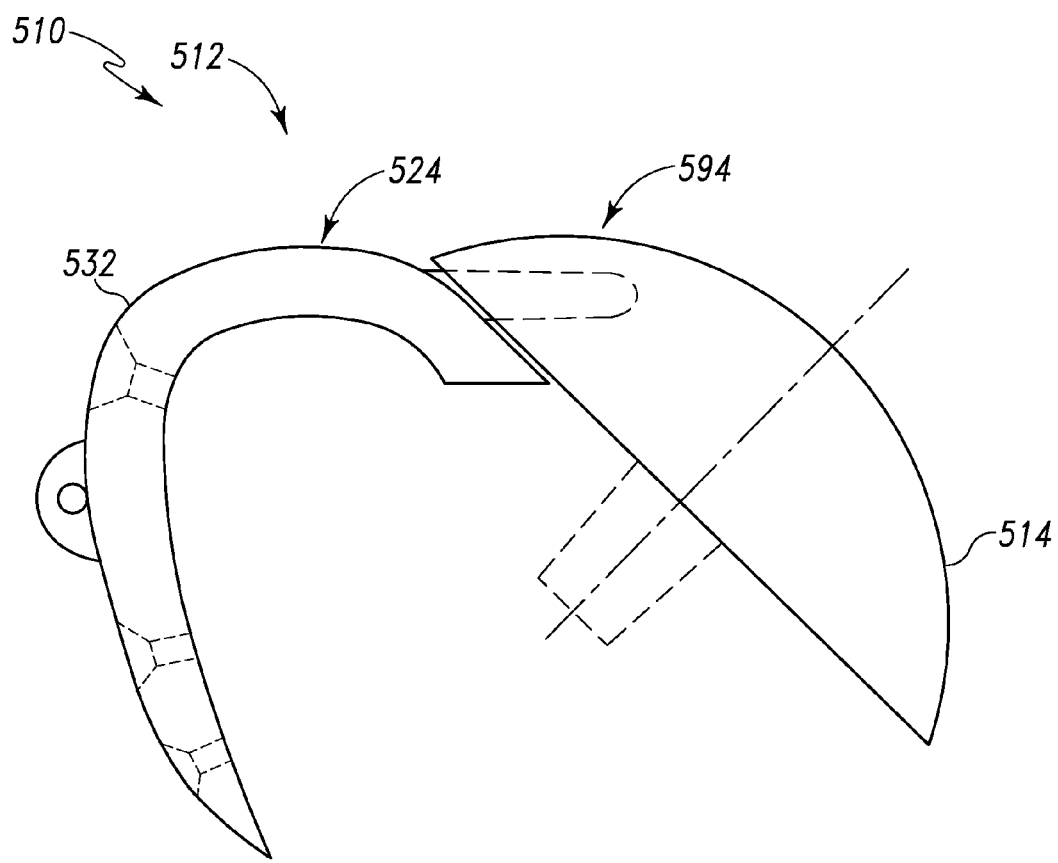
FIG. 26 is a plan view of an assembly of the head of the prosthesis of FIG. 23 with the protrusion member of FIG. 25.

Referring now to FIG. 26, head fragment assembly 594 of the stem assembly 512 of the prosthesis 510 is shown. The head fragment assembly 594 includes the fragment component 524 which is secured to head component 514.

Figure 27:
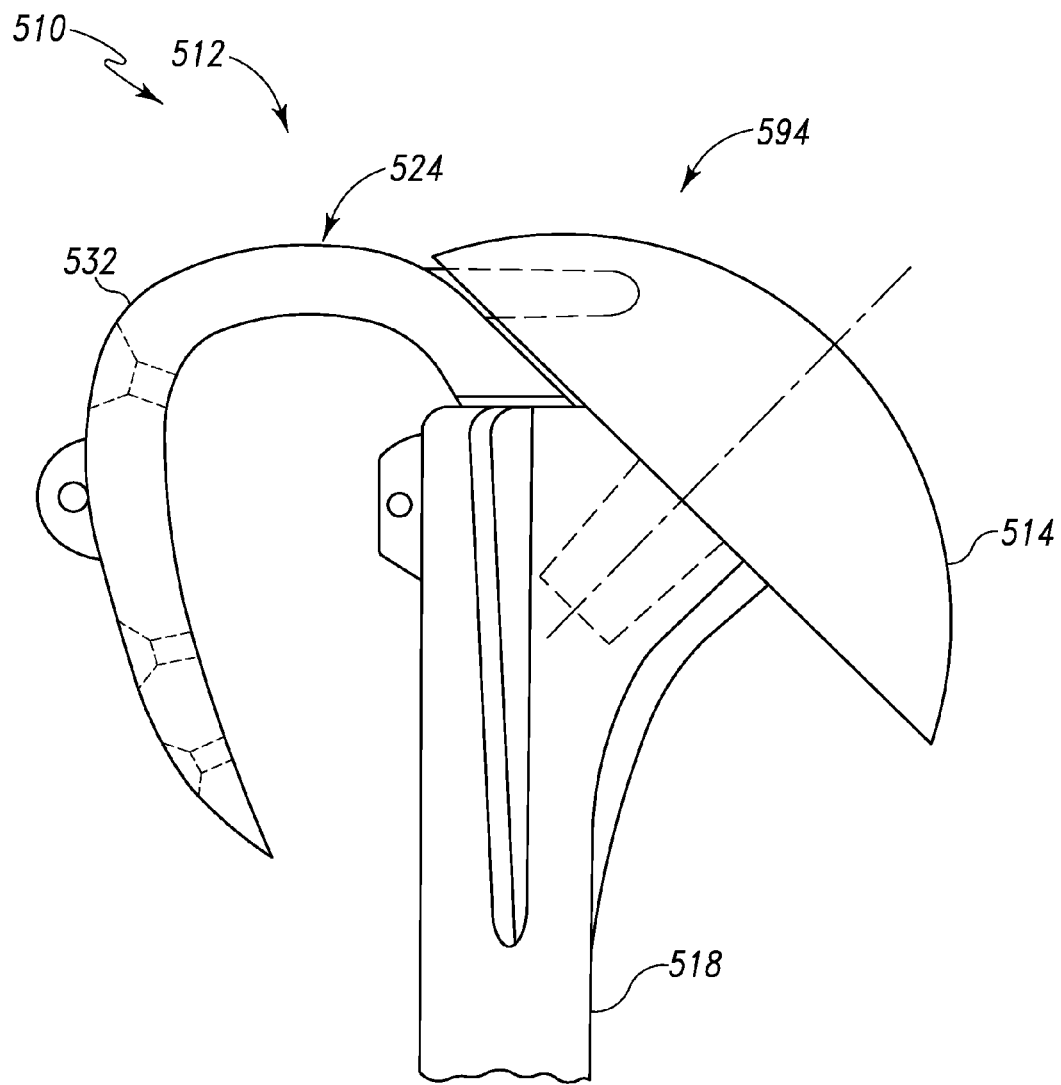
FIG. 27 is a partial plan view of the prosthesis of FIG. 23 showing the area around the protrusion member in greater detail.

Referring now to FIG. 27, the head fragment assembly 594 is shown assembled to the stem component 518 to form stem assembly 512 of the prosthesis 510.

Figure 28:
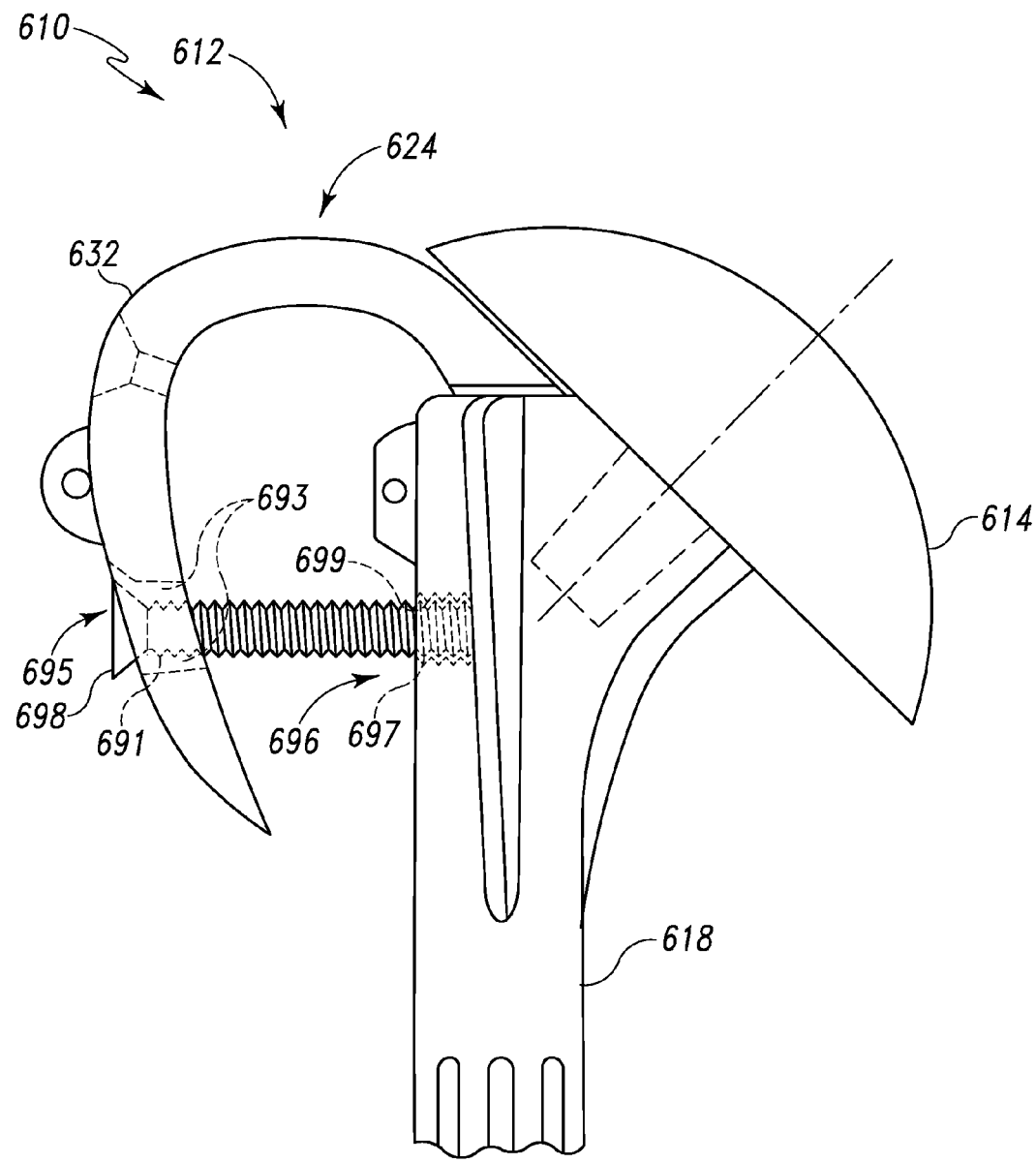
FIG. 28 is a partial plan view of a prosthesis with a rigid fingered protrusion member according to yet another embodiment of the present disclosure.

Referring now to FIG. 28, yet another embodiment of the present disclosure is shown as stem assembly 612 of prosthesis 610. The stem assembly 612 is similar to the stem assembly 112 of FIGS. 9-13 except that the stem assembly 612 includes a fragment component 624 which forms a more rigid connection to the stem 618.

The stem assembly 618 includes a head component 614 similar to the head component 114 of the stem assembly 112 of FIGS. 9-13. The head component 614 is removeably secured to stem component 618. The stem component 618 is similar to the stem component 118 of FIGS. 9-13 except that the stem component 618 further includes an opening 696 for receiving locking screw 698. The locking screw 698 secures finger 632 of the fragment component 624 to stem component 618.

The stem assembly 612 includes the fragment component 624 which is similar to the fragment component 124 of the stem assembly 124 of FIGS. 9-13 except that the fragment component 624 further includes a screw opening 695 for receiving screw 698. The screw 698 secures the finger 632 of the fragment component 624 to the stem component 618. The screw 698 includes head threads 691 which cooperate with internal threads 693 formed in opening 695 of the finger 632 of the fragment component 624. The screw component 698 further includes stem threads 697 which cooperate with internal threads 699 formed in opening 696 of the stem 618. The screw 698 creates a rigid connection of the finger 632 of the fragment component 624 to the stem 618.

Figure 29:
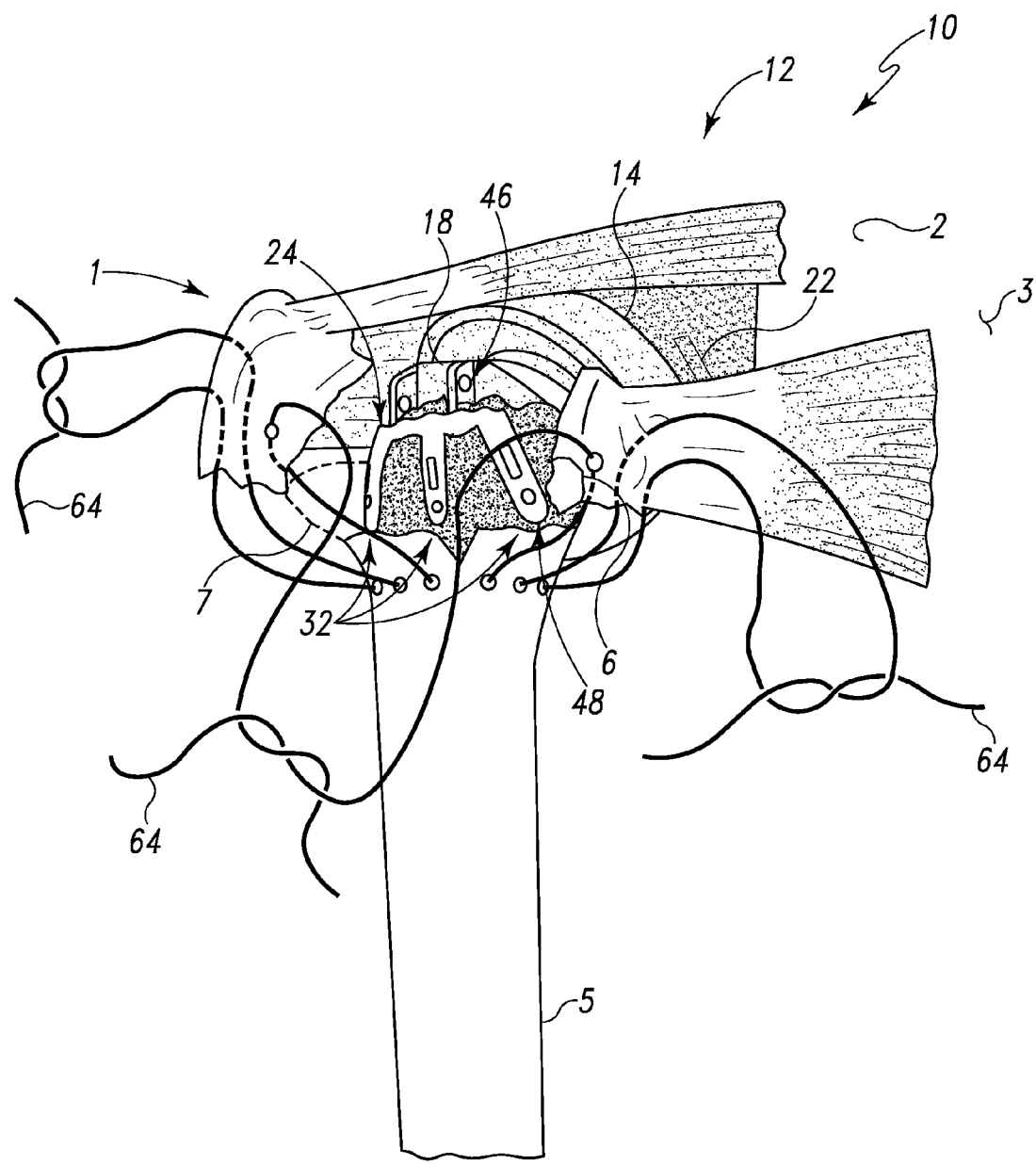
FIG. 29 is a partial perspective view of a shoulder with the prosthesis of the present disclosure showing the use of the opening in the prosthesis to secure sutures and cables.

Referring now to FIG. 29, the prosthesis 10 of FIGS. 2-8 is shown in situ on a shoulder 1 of a patient. The prosthesis 10 includes the stem assembly 12, including stem component 18 which is fitted into humerus 5, as well as head component 14 which cooperates the glenoid component 22 secured to glenoid cavity 2 of scapula 3. The stem assembly 12 of the prosthesis 10 further includes the fragment component 24. The fragment component 24 includes fingers 32 which includes suture openings 48 while stem component 18 includes suture openings 46. Sutures 64 are connected to soft tissue as well as through the holes 46 in the stem component 18 and openings 48 in the fingers 32 of the fragment component 24 to place the fracture, for example four part humeral fracture into reduction to promote union and healing of the fracture.

Figure 30:
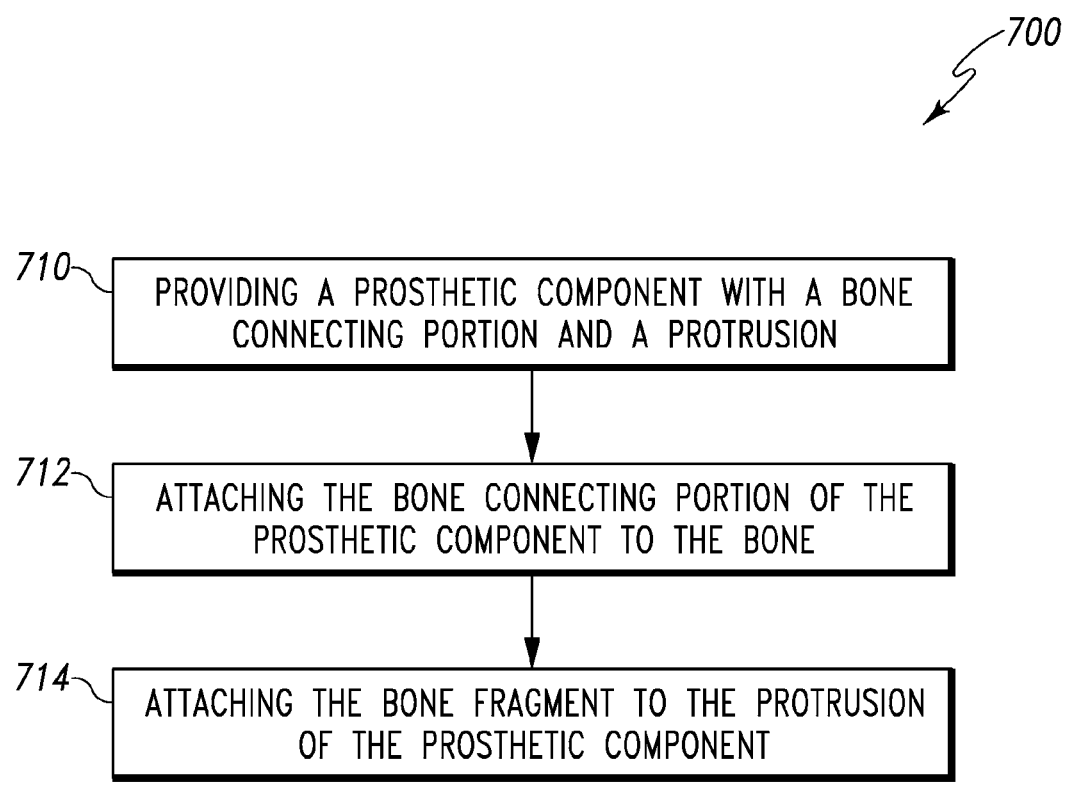
FIG. 30 is a flow chart of a surgical procedure according to another embodiment of the present disclosure.

Referring now to FIG. 30, yet another embodiment of the present disclosure is shown as surgical procedure 700 for performing joint arthroplasty on a patient with a bone fragment at least partially separated from the bone. The surgical procedure 700 includes providing a prosthetic component with a bone connecting portion and a protrusion (block 710). The method 700 further includes attaching the bone connecting portion of the prosthetic component to the bone (block 712). The method 700 further includes attaching the bone fragment to the protrusion of the prosthetic component (block 714).

Although the present invention and its advantages have been described in detail, it should be understood that various changes, substitutions, and alterations can be made therein without departing from the spirit and scope of the present disclosure.

We claim:

1. A method of performing joint arthroplasty on a patient with a bone fragment of a bone at least partially separated from the bone, said method comprising:
    implanting a bone connecting portion of a prosthetic component in the bone;
    connecting a bone fragment portion of the prosthetic component to the bone connecting portion, the bone fragment portion including (I) a connector that connects the bone fragment portion to an end portion of the bone connecting portion and (ii) a first finger having a tip, the first finger extending outwardly from the connector and back toward the bone to position the tip proximate the exterior surface of the bone, the tip including a bone contact surface arranged to face an outer surface of the bone; and positioning the bone fragment between the bone contact surface on the tip of the first finger and the outer surface of the bone, the first finger being configured to press the bone fragment against the outer surface of the bone when the bone fragment portion is connected to the bone connecting portion.

2. The method of claim 1, wherein the bone contact surface of the bone fragment portion includes a barb.

3. The method of claim 1:
wherein the bone includes a second bone fragment at least partially separated from the bone; and further comprising attaching the second bone fragment to the bone using the bone fragment portion by positioning the second bone fragment between a bone contact surface on a tip of a second finger and the outer surface of the bone, the second finger being spaced apart from the first finger and configured to press the second bone fragment against the outer surface of the bone when the bone fragment portion is connected to the bone connecting portion.

4. The method of claim 1, wherein the bone connecting portion comprises a stem portion, the method further comprising:
preparing an intramedullary canal of the bone for the stem portion of the prosthetic component.

5. The method of claim 4, wherein the connector of the bone fragment portion comprises a tapered portion, and
wherein the bone fragment portion is connected to the bone connecting portion matingly fitting the tapered portion of the bone fragment portion with a tapered portion of the stem portion.

6. The method of claim 4, further comprising:
attaching a head component to the stem portion.

7. The method of claim 4, wherein the first finger is configured to bias the bone fragment toward the outer surface of the bone.

* * * * *